(12) United States Patent
Törnblom

(10) Patent No.: US 10,449,351 B2
(45) Date of Patent: Oct. 22, 2019

(54) VALVE FOR ADMINISTRATION OF MULTIPLE DRUG FLUIDS

(71) Applicant: CYT0365 AB, Helsingborg (SE)

(72) Inventor: Micael Törnblom, Helsingborg (SE)

(73) Assignee: CYTO365 AB (SE)

( * ) Notice: Subject to any disclaimer, the term of this patent is extended or adjusted under 35 U.S.C. 154(b) by 98 days.

(21) Appl. No.: 15/506,436

(22) PCT Filed: Sep. 10, 2014

(86) PCT No.: PCT/EP2014/069278
§ 371 (c)(1),
(2) Date: Feb. 24, 2017

(87) PCT Pub. No.: WO2016/037648
PCT Pub. Date: Mar. 17, 2016

(65) Prior Publication Data
US 2017/0246443 A1 Aug. 31, 2017

(51) Int. Cl.
*A61M 39/22* (2006.01)
*F16K 11/083* (2006.01)
(Continued)

(52) U.S. Cl.
CPC ........ *A61M 39/223* (2013.01); *A61M 39/225* (2013.01); *A61M 39/24* (2013.01);
(Continued)

(58) Field of Classification Search
None
See application file for complete search history.

(56) References Cited

U.S. PATENT DOCUMENTS 2,854,027 A * 9/1958 Kaiser ................ A61M 39/223
137/315.25
3,618,637 A * 11/1971 Santomieri ......... A61M 39/223
137/625.11
(Continued)

FOREIGN PATENT DOCUMENTS

DE 3503044 A1 7/1986
WO 2013/055278 A1 4/2013

OTHER PUBLICATIONS

PCT International Search Report dated Nov. 24, 2014 from corresponding Appln. No. PCT/EP2014/069278, 4 pages.
(Continued)

*Primary Examiner* — Jessica Cahill
*Assistant Examiner* — Daphne M Barry
(74) *Attorney, Agent, or Firm* — Dilworth IP, LLC

(57) ABSTRACT

A drug administration valve (100) comprises a valve housing (200) having a plurality of drug inlets (D1 to D4) for receiving drug fluids, such as cytostatic, one flushing inlet (F) for receiving a flushing fluid, and an outlet (O). A valve member (300) rotationally arranged in the housing has a passageway (320; 321) presenting a single inlet (322) and a single outlet (324). The valve member (300) presents a plurality of drug positions for guiding an associated drug fluid to the outlet (O), and one or more flushing positions for guiding a flushing fluid through the same passageway (320; 321) as the drug fluids in order to flush said passageway (320; 321) from any drug residuals. The valve member (300) is prevented from rotating from one drug position to another drug position without passing one of said flushing positions.

13 Claims, 23 Drawing Sheets

(51) Int. Cl.
*F16K 11/085* (2006.01)
*A61M 39/24* (2006.01)

(52) U.S. Cl.
CPC .......... *F16K 11/083* (2013.01); *F16K 11/085* (2013.01); *A61M 2039/229* (2013.01); *A61M 2205/582* (2013.01)

(56) References Cited

U.S. PATENT DOCUMENTS

| | | | | |
|---|---|---|---|---|
| 3,957,082 A * | 5/1976 | Fuson | ................. | A61M 5/1408 137/625.41 |
| 4,219,021 A * | 8/1980 | Fink | .................... | A61M 39/223 137/556.6 |
| 4,604,093 A * | 8/1986 | Brown | .............. | A61M 5/16827 137/625.11 |
| 7,896,864 B2 * | 3/2011 | Lockwood | .......... | A61M 1/0031 604/541 |
| 2017/0258991 A1 * | 9/2017 | Tornblom | ........... | A61M 5/1409 |

OTHER PUBLICATIONS

PCT International Preliminary Report on Patentability dated Apr. 9, 2015 from corresponding Appln. No. PCT/EP2014/069278, 6 pages.

* cited by examiner

Section A-A

Section A-A

Section B-B

Section C-C

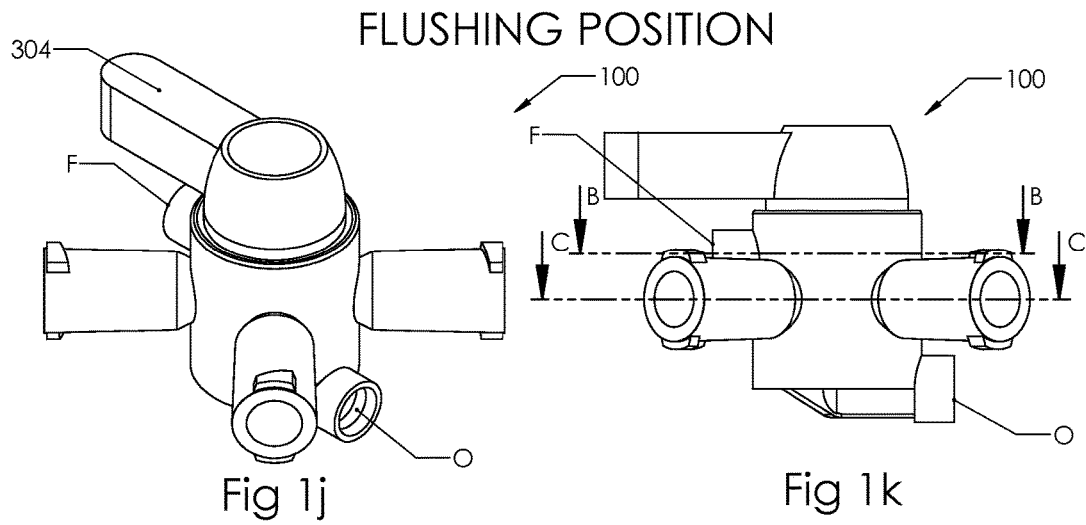
FLUSHING POSITION
Fig 1j
Fig 1k
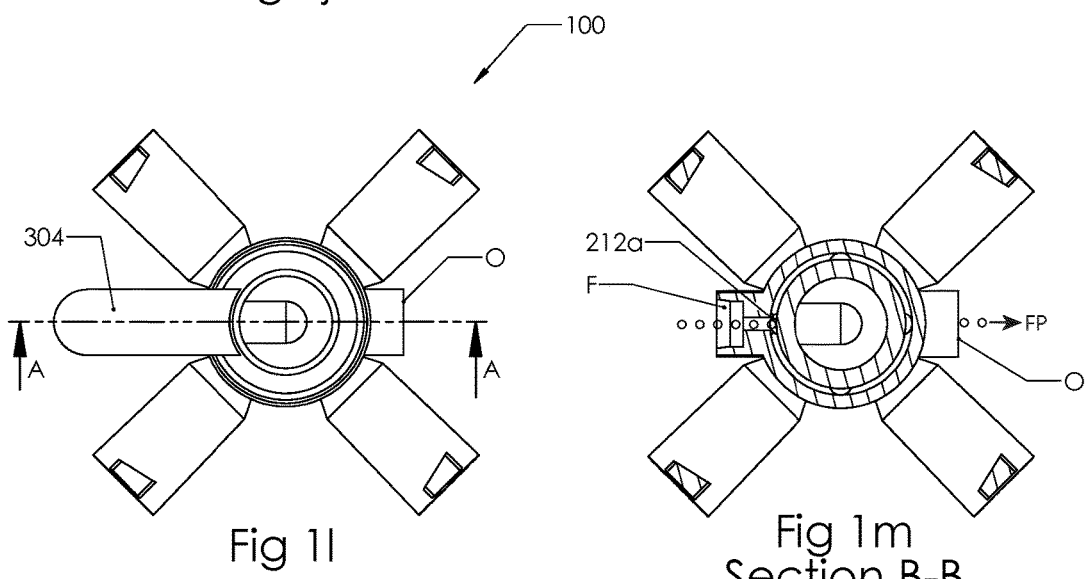
Fig 1l
Fig 1m
Section B-B
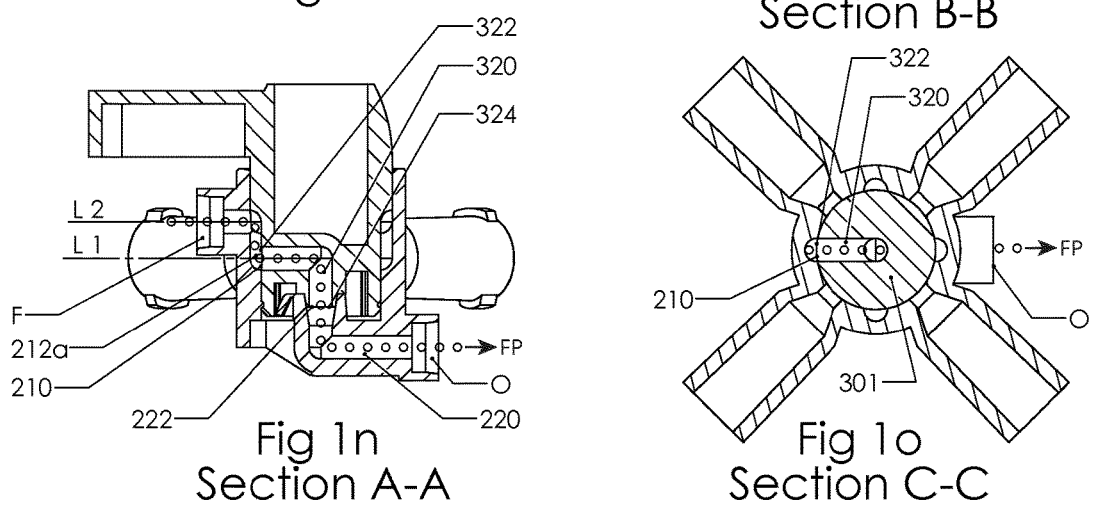
Fig 1n
Section A-A
Fig 1o
Section C-C

DRUG POSITION

Section B-B

Section A-A

Section C-C

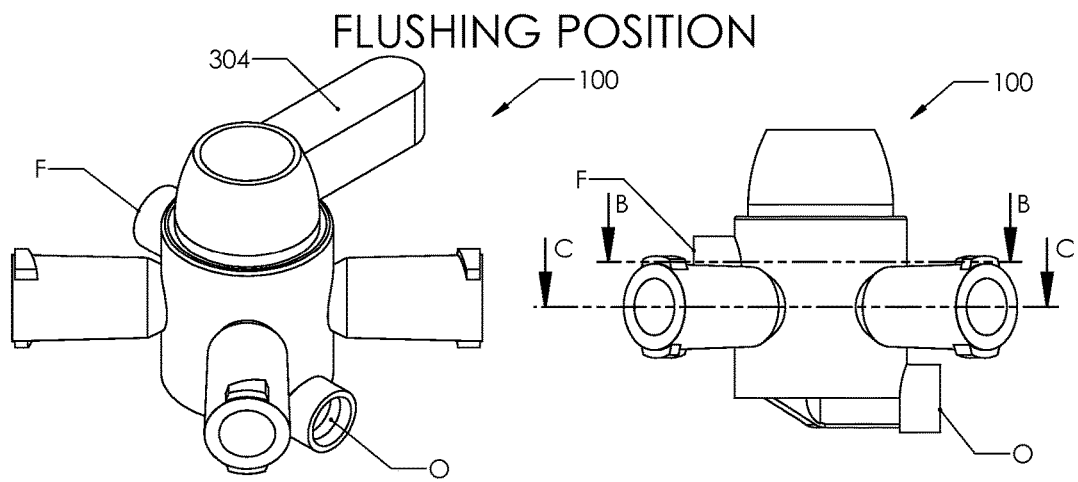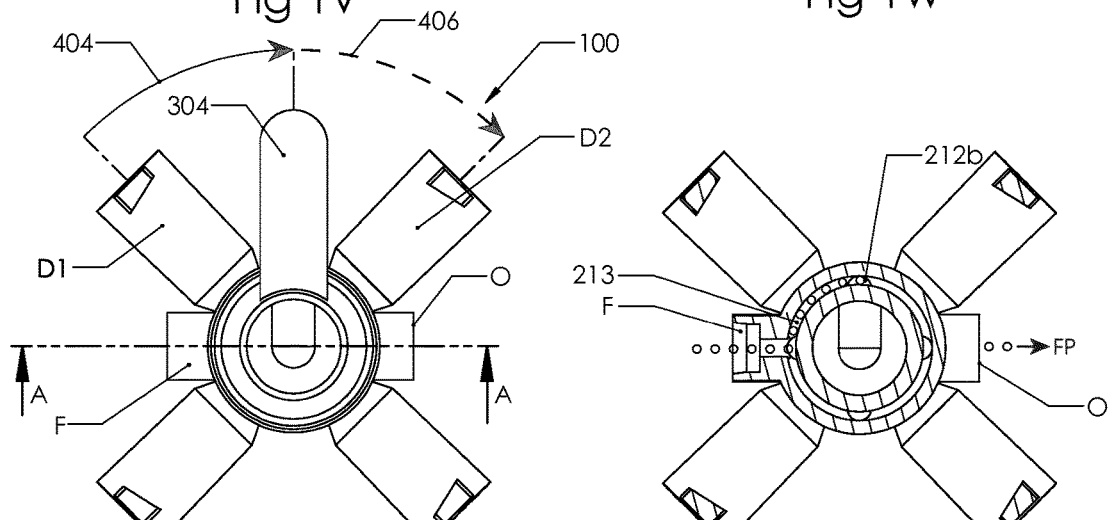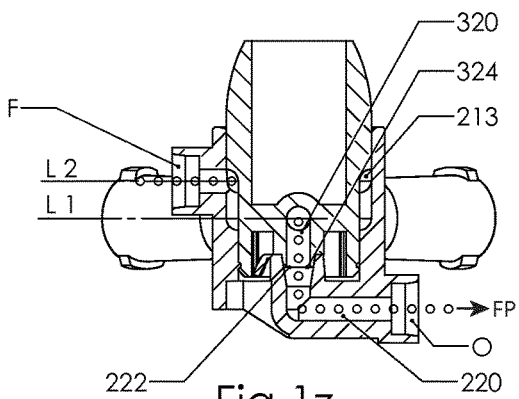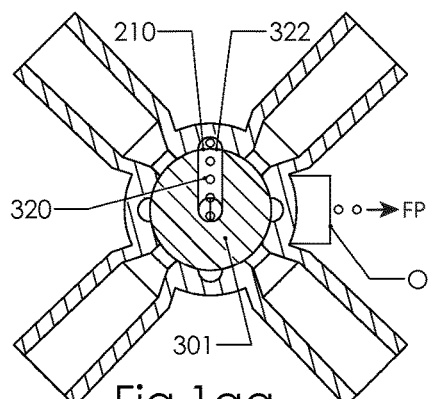

Section A-A

Section A-A

Section B-B

Section C-C

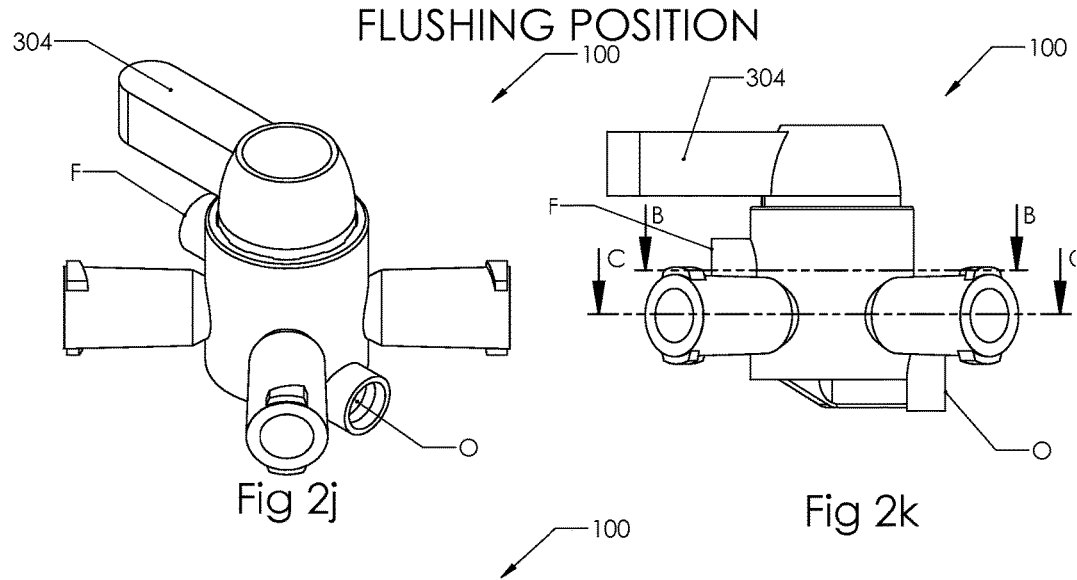
Fig 2j
Fig 2k
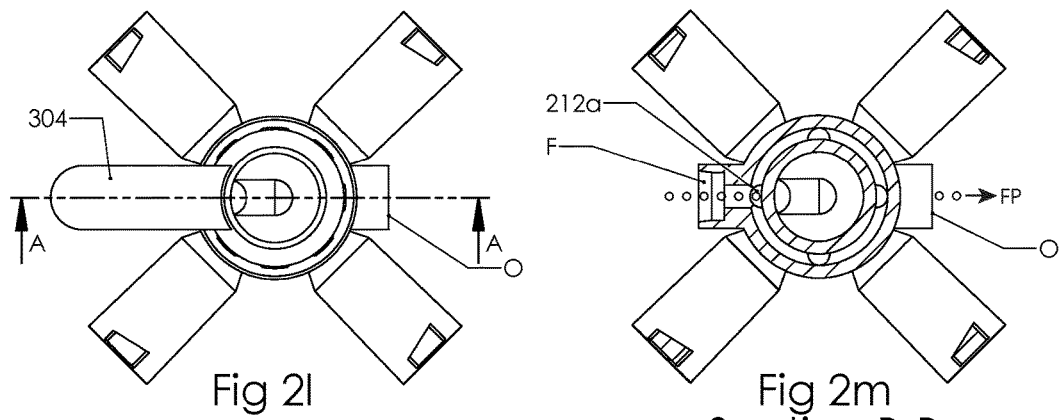
Fig 2l
Fig 2m
Section B-B
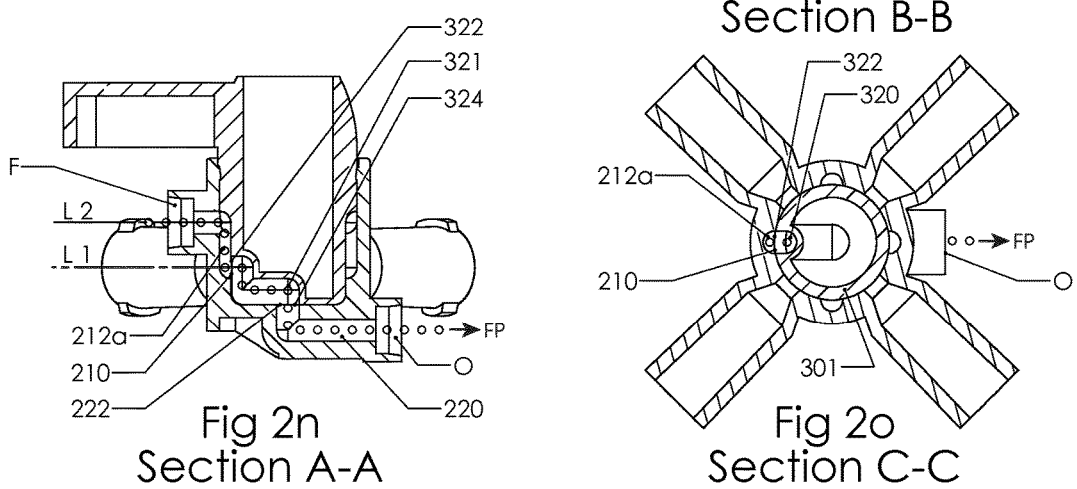
Fig 2n
Section A-A
Fig 2o
Section C-C

DRUG POSITION

Section B-B

Section A-A

Section C-C

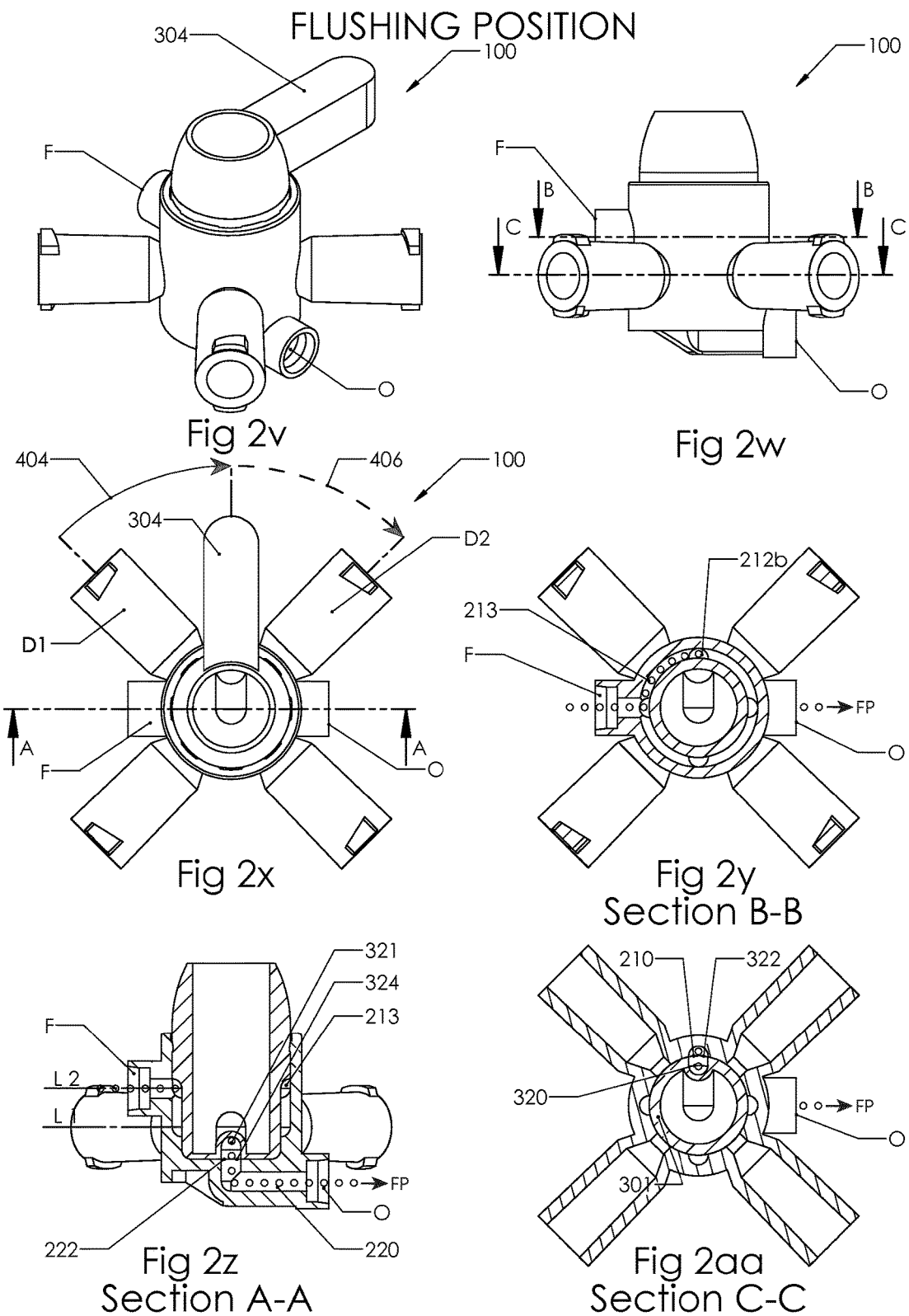

Section A-A

Section A-A

Section B-B

Section C-C

FLUSHING POSITION

Section B-B

Section A-A

Section C-C

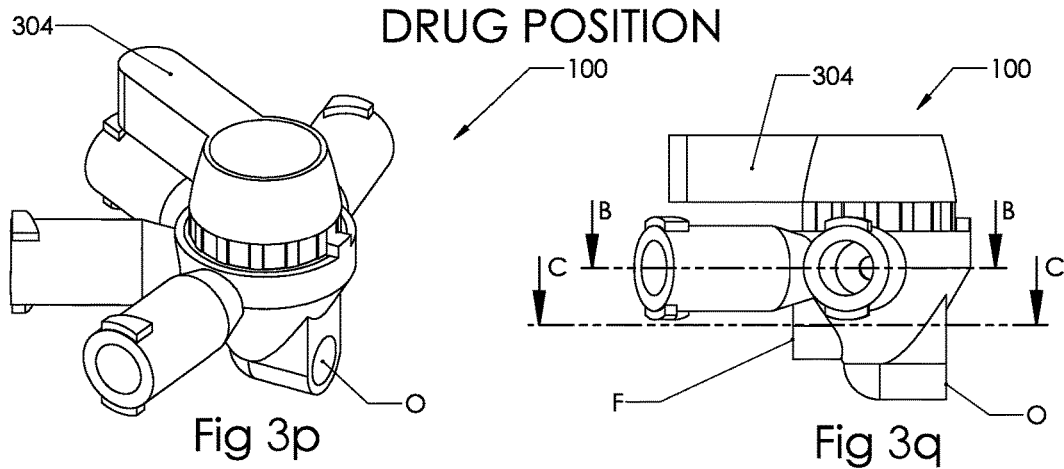
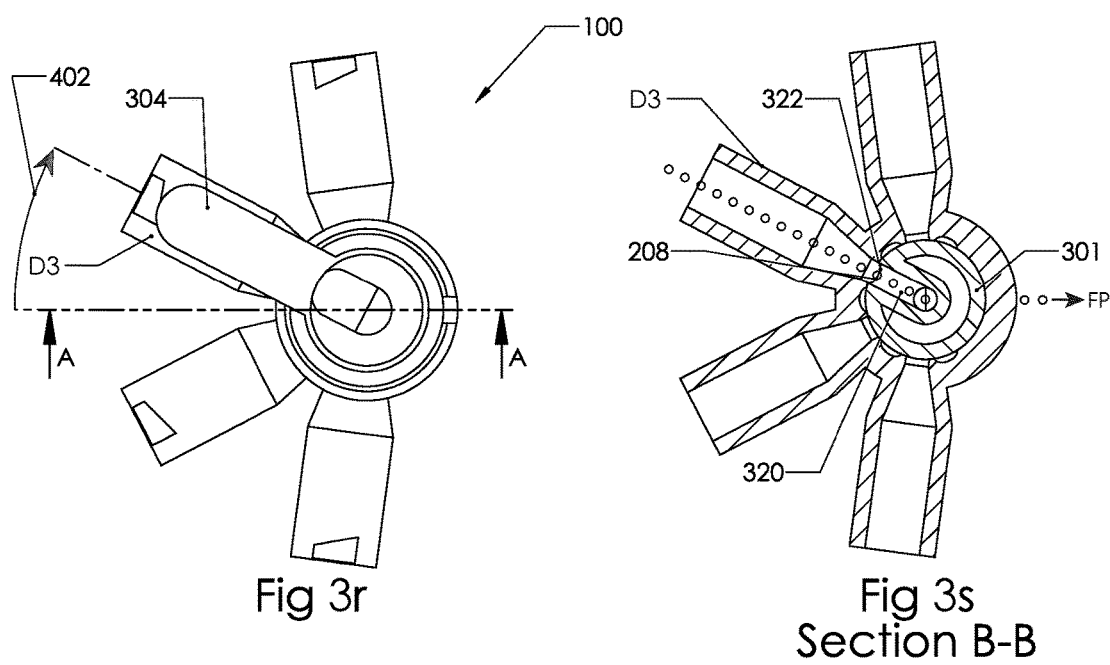
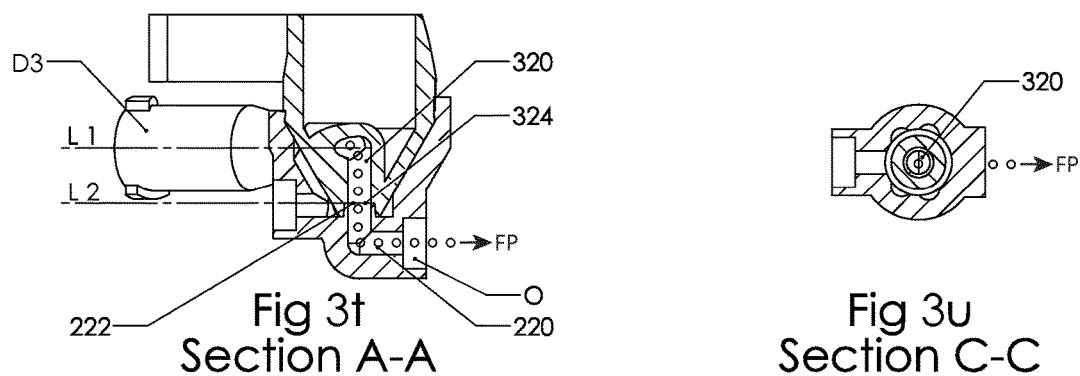

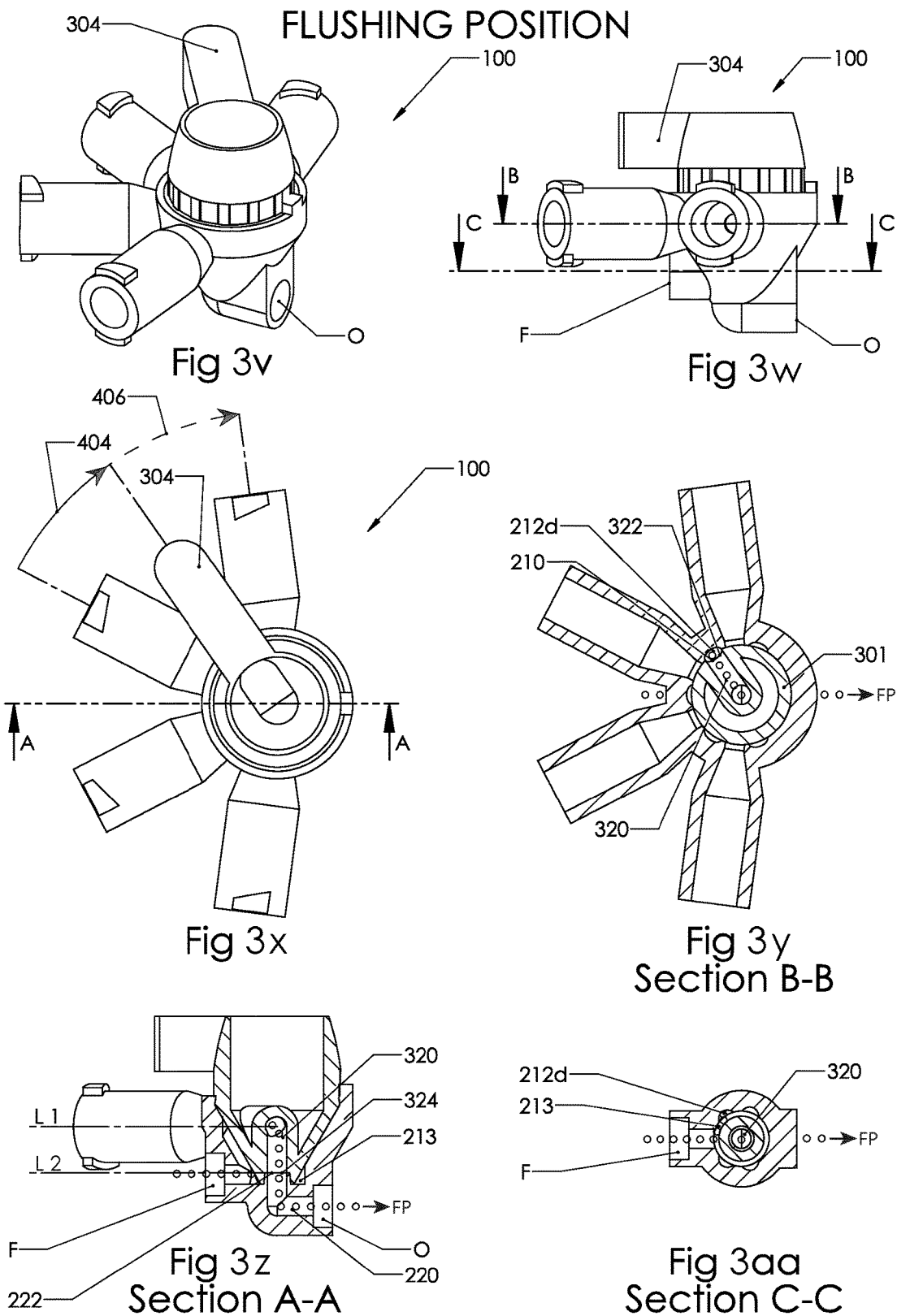

Section A-A

Section B-B

Section C-C

FLUSHING POSITION

Section A-A

Section B-B

DRUG POSITION

Section A-A

Section B-B

VALVE FOR ADMINISTRATION OF MULTIPLE DRUG FLUIDS

FIELD OF THE INVENTION

The present invention relates to administration of drug fluids. More specifically, the present inventive concept relates to valves or stopcocks for sequential administration of a plurality of drug fluids, such as cytostatics.

With respect to prior-art multi-drug valves, there are plenty of medical situations in which a multiple of drug fluids to be inserted into a patient has to be handled. Typically, the various drug fluids are selected and branched by means of a drug-fluid valve. Moreover, in chemotherapy it is often of utmost importance to handle drug fluids to a patient which is treated for cancer in a reliable and safe manner. However, due to stressful working environments, tiredness, the human factor, etc., the handling of these drug fluids, including their connections, dosages, etc. may lead to errors. For example, there is a need to clearly separate different fluids from each other, since they may chemically react in an undesired manner.

Applicant's WO 2013/055278 discloses a multiple-drug valve for administration of a plurality of drug fluids, such as cytostatics. This known multiple-drug valve comprises a housing having a plurality of circumferentially distributed primary inlets for receiving a respective one of the drug fluids and a secondary inlet for receiving a secondary fluid, such as a neutral fluid. The valve has an outlet from which the fluids will be directed to the patient. A rotary valve member is arranged in the housing. The housing has a plurality of primary valve positions in each of which an associated one of the primary inlets is connected to the outlet, and a plurality of intermediary valve positions in each of which the secondary inlet is connected to the outlet. Moreover, the valve member has an outer surface sealingly engaging an inner surface of the housing, such that the primary and secondary inlets are sealingly connected to openings arranged in the outer surface of the valve member in each of the primary and intermediary valve positions, respectively.

U.S. Pat. No. 4,758,235 discloses a system for administration of a plurality of drug fluids. A drawback of this system is that it allows the user to shift from one drug position to another drug position without any flushing.

Parallel infusion of drugs is generally not allowed, nor temporary mixing of drug fluids due to drug fluid residuals in the rotatable valve member.

SUMMARY OF INVENTION

It is an object of the invention to provide an enhanced valve for sequential administration of a plurality of drug fluids with an efficient flushing of the valve between the each drug fluid administration.

The invention focuses on securing a complete flushing of the valve member's internal volume, eliminating or at least substantially reducing the risk of drug incompatibility within the valve.

According to the inventive concept, there is provided a valve for administration of two or more drug fluids, such as cytostatics, said valve comprising:
a valve housing having:
an inner circumferential surface,
a plurality of drug inlets for receiving said drug fluids and fluidly connected to associated drug outlets arranged at the inner circumferential surface of the housing, and
one flushing inlet for receiving a flushing fluid, such as a neutral fluid, and fluidly connected to one or more flushing outlets arranged at the inner circumferential surface of the housing; and
a valve member having a rotational axis and provided with a passageway presenting a single inlet arranged at an outer circumferential surface of the valve member and a single outlet arranged coaxially with said rotational axis;
wherein the valve member is arranged to be rotated into:
a plurality of drug positions in each of which the single passageway inlet is fluidly connected to a respective one of said drug outlets for guiding an associated drug fluid via a flow path defined by said passageway to said passageway outlet, and
one or more flushing positions in which the single passageway inlet is fluidly connected to a respective one of said one or more flushing outlets for guiding said flushing fluid through the same flow path defined by said passageway in order to flush said passageway from any drug residuals, and
wherein the valve member is prevented from rotating from one drug position to another drug position without passing one of said flushing positions.

Preferred embodiments of the invention are set out in the dependent claims.

In operation, the user would normally rotate the valve member in sequence as follows:

Optional Priming→Drug position #1→Flushing position→Drug position #2→Flushing position-→Drug position #3→etc.

The invention presents the following features and advantages:
Going from one drug position to the next drug position in the sequence, the interior of the valve member's fluid passageway will be efficiently flushed from any drug fluid residuals. It is not possible for the user to set aside this security feature of the valve.
The same fluid passageway in the valve member is used for both drug fluids and the flushing fluid.
The house (optionally in combination with the valve element) is designed to distribute the flushing fluid to one or more flushing positions between each drug positions.
The valve member receives drug fluids and a flushing fluid from each drug position and each flushing position by rotation of the valve member around its rotational axis.
All the drugs to be used may be connected to their respective drug inlets before use of the valve. Thereby, the infusion set may be prepared before the patient arrives or in another room with a sterile and safe environment in order to avoid the risk of leakage and contamination, which is a convenience and safety factor for both nurses and patient. Flow through the valve may be prevented by arranging closed valve positions and/or by using one or more flow stop devices such as unlimited examples of tubing clamps, pinch clamps, roller clamps in the inlet and/or the outlet side of the valve.
The different valve positions are preferably predetermined positions and are preferably identifiable by the user. This may be done by the shape of a handle member and/or by arranging a tactile response to a user at each valve position so the operator can sense the correct position ("click indication").

The valve is preferably intended for one complete treatment use. The housing and the valve member may be manufactured by means of molding, such as injection molding. More specifically, the housing and the valve member may each be manufactured in a single piece.

Terminology

The term "drug fluid" as used herein is to be interpreted in a wide sense and should not be limited to pure drugs. Drug fluids may include various types of cytostatics which are to be infused into the vascular system of a patient intravenously in order to treat her/him from cancer. Other fluids which may be administered by the present inventive valve include volume expanders, blood-based products, blood substitutes, medications, nutritional solutions, antibiotics etc.

The term flushing fluid is to be interpreted as any suitable fluid to be administered to the patient and/or for priming/flushing purposes. Especially, the flushing fluid may be a neutral fluid, such as a saline solution.

The term fluid passageway should be construed as including channels in the form of a bore having defined end openings, open recess configurations, or combinations thereof.

The term "drug position" is to be construed as an intended position of the valve member different from the flushing position(s) in which a drug fluid may be administered from a drug inlet to the outlet of the valve.

The term flushing position is to be interpreted as an intended position of the valve member, different from the drug positions, in which a flushing fluid may be administered from the flushing inlet to the outlet of the valve.

The flushing position is the position in which saline may be administered to the patient. The first flushing position may be used to prepare the patients vein before the infusion therapy starts to verify that the infusion works properly before the drugs are administered. The subsequent flushing positions may be used to dilute the infused drug with the patients' blood stream.

The term "flushing" as used herein is to be construed as the operation performed for cleaning the valve or parts thereof from previously administered drugs, especially the fluid passageway of the valve member.

The term "priming" as used herein is to be construed as an operation performed for removing air from the valve and providing a fluid-filled valve.

The term "closed position" should be construed as a position where there is no fluid connection between the valve inlets and the valve outlet. A closed position may be present between a flushing position and a drug position and/or between two flushing positions.

The term "transition position" should be construed as a position where a drug inlet and a flushing inlet are in fluid communication with the valve outlet at the same time. The transition position may be a static position or a transition between a flushing and a drug position.

Other features and advantages of embodiments of the present invention will become apparent to those skilled in the art upon review of the following drawings, the detailed description, and the appended claims.

BRIEF DESCRIPTION OF THE DRAWINGS

The inventive concept, some non-limiting embodiments and further advantages of the inventive concept will now be further described with reference to the drawings.

Each embodiment is illustrated with a number of figures marked with letters (e.g.

FIG. 1 illustrates a first embodiment of a 4-drug valve.

Figure 1A:
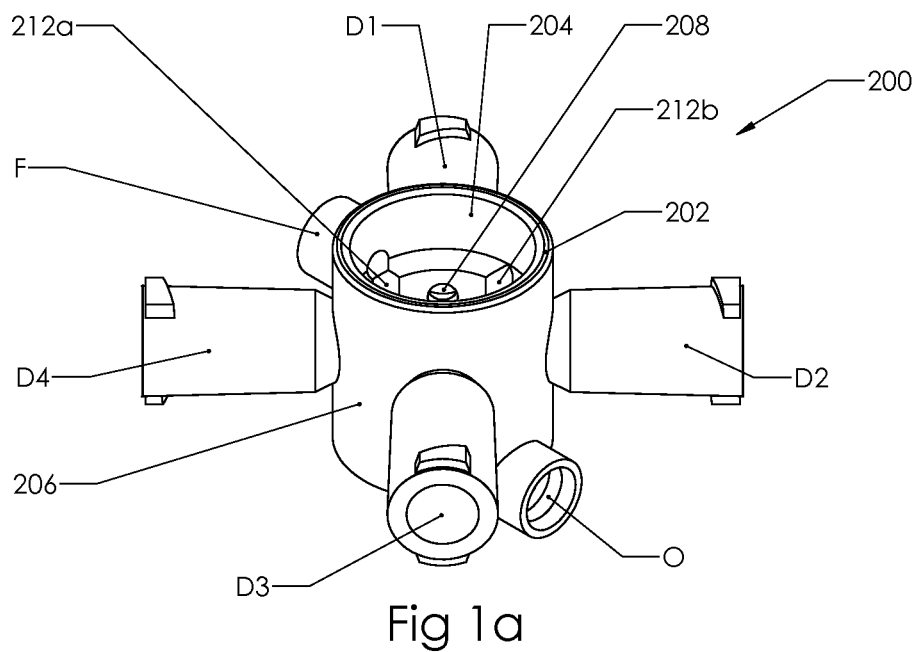
FIG. 1a, FIG. 1b, etc for the first embodiment). In the following, any reference to the figure number only (e.g.
Figure 1B:
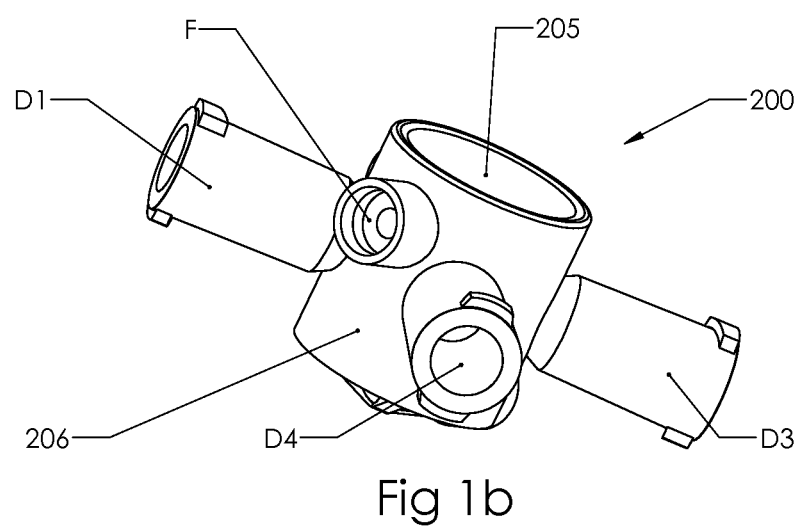

The present inventive concept relates to disposable valves for administration of drug fluids. For example, the drug fluids may include various types of cytostatics which are to be infused into the vascular system of a patient intravenously in order to treat her/him from cancer. Other fluids which may be administered by the present inventive valve include volume expanders, blood-based products, blood substitutes, medications, nutritional solutions, etc.

In one example, a drip chamber may be provided before the valve. Preferably, one drip chamber is provided in connection to each bag storing the fluids. In another example, a drip chamber may be provided downstream the valve. The advantage of using a drip chamber downstream the valve is that only one drip chamber is necessary.

In addition, a booster pump may be utilized to pre-set a flow rate by a predetermined pressure in the tube. In one example, the booster pump is provided before the valve. In another example, the booster pump is provided after the valve.

Some embodiments may be used together with and/or have integrated backflow valves. Backflow valves may be used (i) to prevent backflow (reflux) in the tubing which is presently used for administration, and (ii) to prevent backflow in other tubings fluidly connected by the valve.

In one example, the flushing tubing may have a backflow valve. In another example, a backflow valve may be arranged on each drug tubing. In another configuration, backflow valves may be integrated in the valve inlets. Yet in another example, a backflow valve may be integrated in the fluid passageway of the valve member. In still another example, a backflow valve may be integrated in the valve outlet or arranged on an outlet tubing.

It may also be an advantage to use backflow valves with an elastomeric connector element allowing the valve to be a closed system before connection and/or after disconnection of inlets.

However, such need for separate backflow valves may be avoided if the inventive valve is configured such that circumferentially adjacent flushing and drug positions are sufficiently spaced in the rotational direction.

First Embodiment of a 4-Drug Valve (FIG. 1)

Reference is now made to FIG. 1 showing a first embodiment of a 4-drug valve or stopcock 100 according to the inventive concept for the administration of up to four different drug fluids. This embodiment comprises four drug positions and four flushing positions.

The valve 100 comprises a cylindrical housing 200 (FIGS. 1a to 1d) and a valve member 300 (FIGS. 1e to 1i). A cylindrical body 301 of the valve member is rotatably arranged in a cylindrical cavity of the housing 200. By cylindrical is here meant a cylinder shape with constant radius. The housing 200 and the valve member body 301 may have shapes other than cylindrical. For example, they may be frusto-conical, comprised of several frusto-conical parts, etc as will be described in connection with other embodiments.

In the assembled valve 100 (FIG. 1j and forward), an outer cylindrical surface 302 of the valve member body 301 sealingly engages with an inner cylindrical surface 204 of the housing 200, thereby creating an assembly which is airtight and prevents the flow of fluids. The diameter of the outer cylindrical valve member surface 302 may be slightly larger than the inner cylindrical housing surface 204 in order to create the sealed engagement.

Alternatively, other ways of engaging sealingly is conceivable. In one example, a sealing element (not shown) may be arranged in between the outer cylindrical valve member surface 302 and the inner cylindrical housing surface 204. For example, the sealing element may be made of a thin, flexible material which may be fitted snugly between the valve member and the housing. For example, the sealing member may be an O-ring.

Reference numeral 207 indicates an inwardly directed flange or rim on the inner surface of the housing. Reference numeral 307 indicates a corresponding annular recess in the valve body 301 which receives the flange 207 in the assembled state in order to maintain the valve member 300 in the housing 200.

The housing 200 and the valve member 300 may be fabricated in any material which does not react chemically to any considerably extent with the intended drug fluids to be used, and which thereby and also in other aspects is suitable for medical applications. Moreover, the material must be suitable for sterile environments. Examples of materials include plastic materials. The plastic material may be transparent or opaque depending on the medical application.

The housing 200 may be fabricated in the same material as the valve member 300. Alternatively, the housing 200 may be fabricated in a material which is different from that of the valve member 300. In particular, the material of the housing 200 and the valve member may have different hardness. Different hardness may be used for providing the tactile feedback means.

Different hardness and different material may also be used for providing improved sealing engagement.

The housing 200 illustrated in FIGS. 1a to 1d comprises a housing wall 202 enclosing an inner cylindrical housing cavity 205 into which the cylindrical valve member body 301 is to be inserted. The cylindrical housing wall 202 comprises an outer circumferential surface 206 and said inner cylindrical surface 204.

A valve according to the inventive concept generally comprises a plurality of drug inlets D1, D2, etc and a single flushing inlet F, all arranged at the outer housing surface 206. In this embodiment there are four drug inlets D1 to D4 arranged at a first level L1 with respect to the rotational axis and a single flushing inlet F arranged at a second level L2 axially above the drug inlet level L1 (FIG. 1d).

The four drug inlets D1 to D4 are fluidly connected to the inner housing cavity 205 at separate outlets 208 and may be integrally formed with the cylindrical housing wall 202 and shaped as pipes or studs. In this embodiment, the four drug outlets 208 located at level L1 are angularly spaced at 90 degrees about the rotational axis.

The flushing inlet F at level L2 is arranged between the two drug inlets D4 and D1 and is fluidly connected to the inner housing cavity 205 at a separate flushing outlet 210. As for the drug inlets, the flushing inlet F may be integrally formed with the cylindrical housing wall 202 and shaped as a pipe or stud.

An axially oriented flushing groove 212a is formed in the inner housing surface 204 or the housing wall 202 and extends axially from level L2 down to the flushing outlet at level L1. As shown in FIG. 1d, three additional axial flushing grooves 212b, 212c and 212d are formed in the inner housing surface 204 between the drug inlet pairs D1/D2, D2/D3 and D3/D4.

It will be noted that the above described fluid passageways formed in the housing are so arranged that the drug fluids and the flushing fluid are kept separate from each other when flowing towards the inner housing cavity 205 and the valve member 300.

In operation, the drug positions and the flushing positions of the valve 100 are defined by the angular positions of the drug outlets 208 and the angular positions of the flushing grooves 212a to 212d, respectively.

Figure 1C:
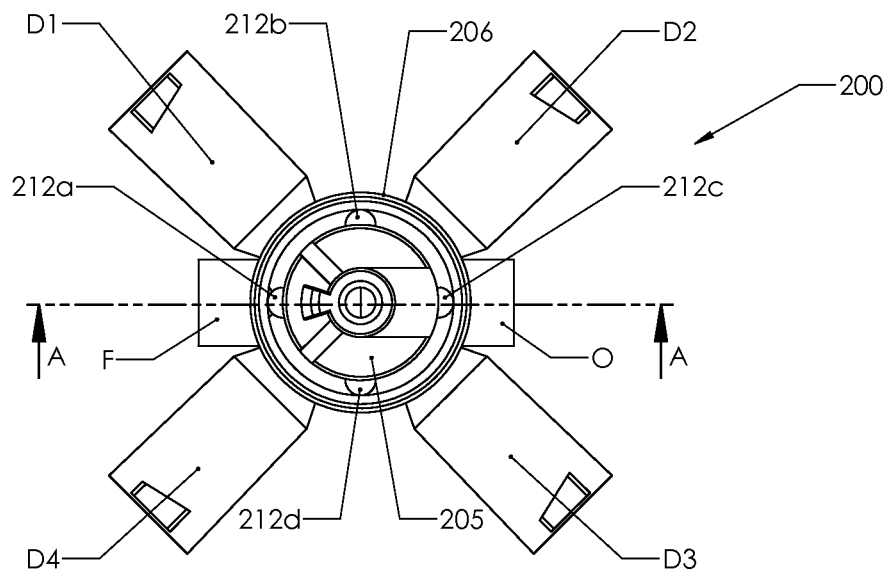
FIG. 1) is a general reference to all the individual figures for the corresponding embodiment.
Figure 1D:
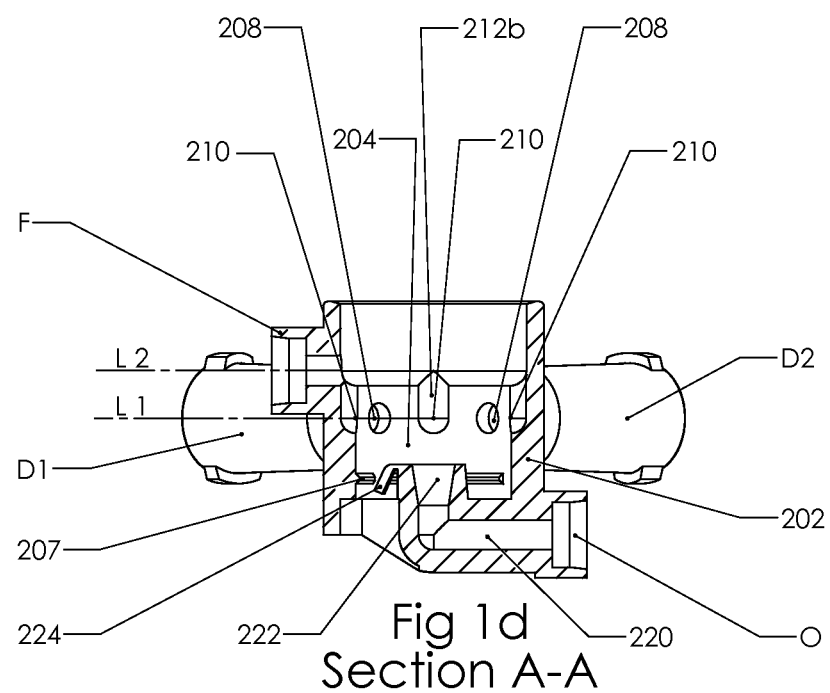

With reference to FIGS. 1c and 1d, the bottom part of the housing 200 includes an outlet O which is fluidly connected to the inner cavity 205 of the housing by means of an bottom channel 220 having a central bottom opening 222 coaxial with the rotational axis.

As shown in FIG. 1d, a resilient lip 224 integrally formed at one side of the bottom opening 222 is arranged to cooperate with the valve member 300 for providing a tactile response to the user indicating the different valve positions.

In use, a neutral fluid, such as a saline solution, or equivalently a saline fluid, may be is led into the flushing inlet F by means of a tube. This neutral fluid, termed "flushing fluid" may comprise a sterile solution of sodium chloride (NaCl). The flushing inlet F may be provided with a connection device for connecting said tube or may be glued to the tube. In a non-limiting example, connection devices comprise male and female Luer connectors. It is clear, however, that any type of connection devices may be used.

The valve member 300 will now be described more in detail with reference FIGS. 1e to 1i. A handle 304 integrally formed with the cylindrical valve member body 301 allows the valve member 300 to be rotated by the user into the eight different valve positions. The radial direction of the handle 304 will in known manner allow the user to identify the present valve position and it will be noted that FIGS. 1j to 1aa illustrating the different valve positions also show the handle position.

The cylindrical valve member body 301 (FIGS. 1e to 1i), being rotatably and sealingly arranged in the housing cavity 205, is provided with a fluid passageway 320 having a single inlet 322 arranged at the outer cylindrical valve member surface 302 and a single outlet 324 arranged coaxially with the rotational axis at the bottom 326 of the valve member 300.

In the embodiment in FIG. 1, the fluid passageway 320 is formed by (i) a radial channel part 320a extending radially from the single inlet 322 towards the rotational axis 400, and (ii) an axial channel part 320b extending coaxially with the rotational axis 400 towards the single outlet 324. In this embodiment, the fluid passageway 320 is in the form of a closed tubular channel with the inlet 322 and outlet 324 in the form of defined openings. Preferably, the single inlet opening 322, the tubular channel 320 and the single outlet opening 324 all have the same circular cross section, resulting in a laminar flow through the passageway. Also, in this embodiment the cross section of the single inlet opening 322 corresponds to the cross section of the drug outlets 208 in the housing. In other embodiments described below, the passageway may be in the form of an open recess or groove.

Figure 1E:
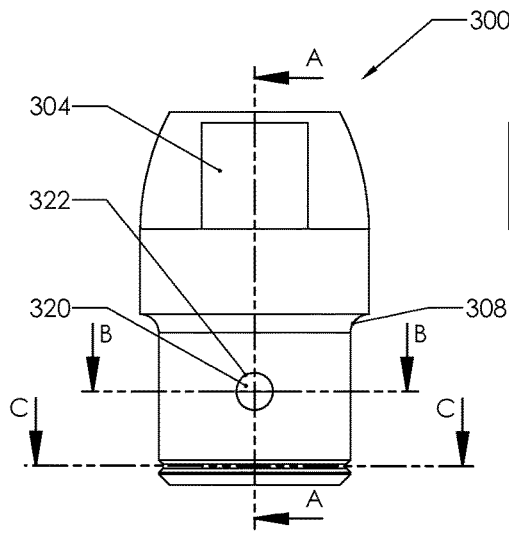
Figure 1F:
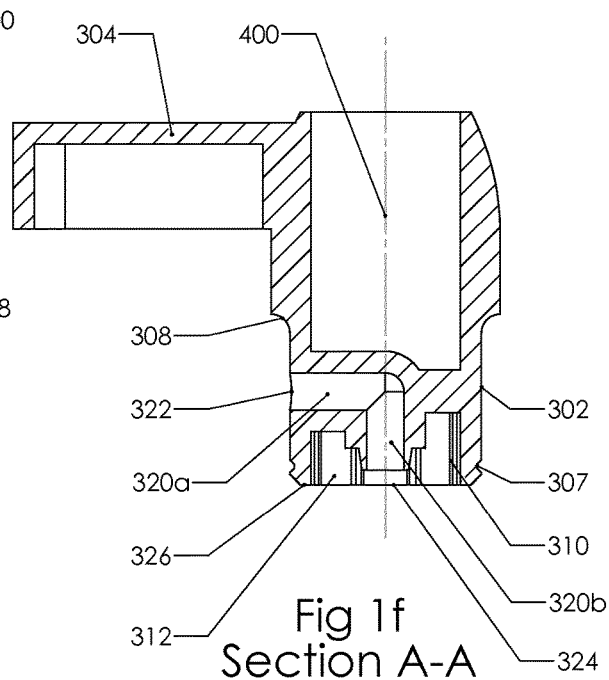
Figure 1G:
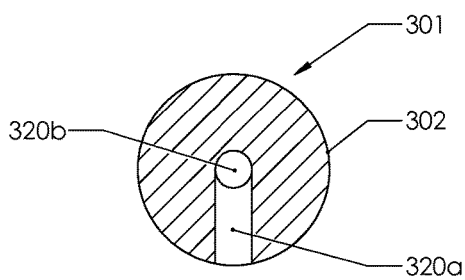
Figure 1H:
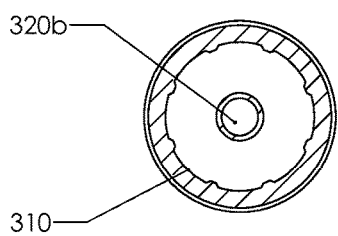
Figure 1I:
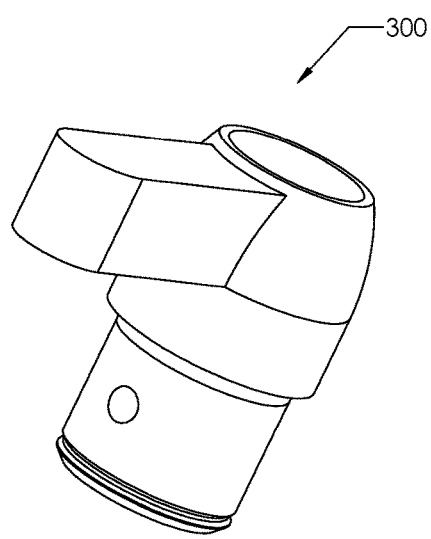
Figure 1P:
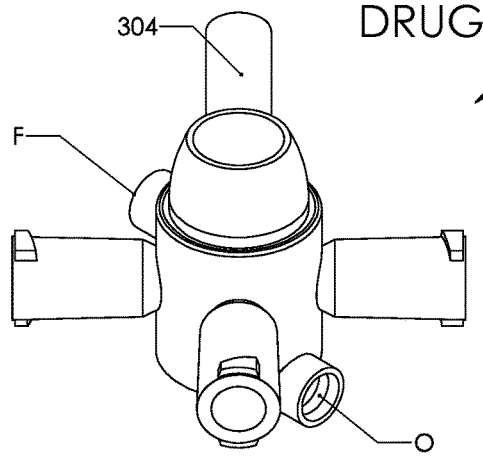
Figure 1Q:
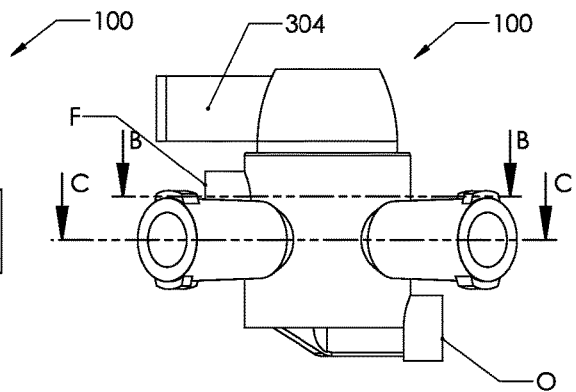
Figure 1R:
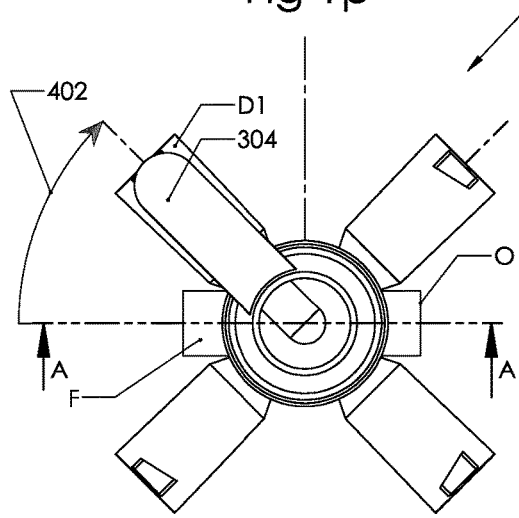
Figure 1S:
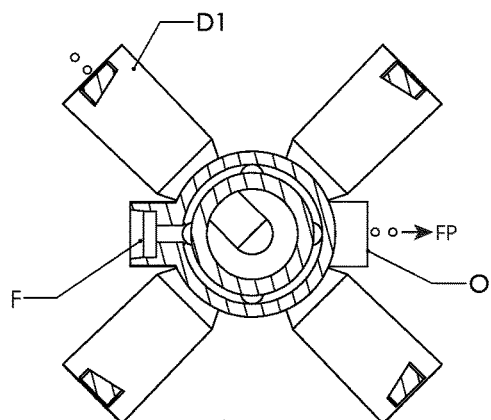
Figure 1T:
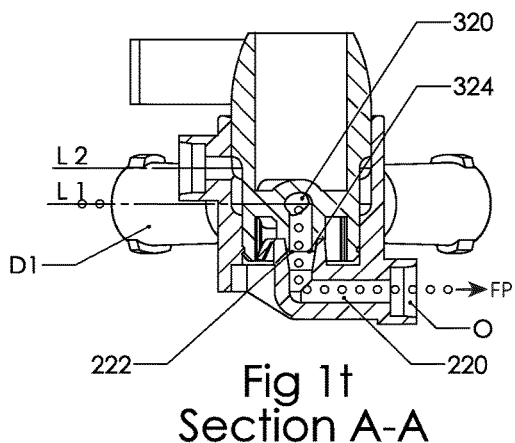

A feature of the valve 100 is that the single flushing inlet F is in permanent fluid connection with each one of the flushing grooves 212a to 212d in order to distribute the flushing fluid to these grooves in the flushing positions of the valve. In the embodiment in FIG. 1, this circumferential distribution is accomplished by means of a circular flushing fluid channel 213, which is located in a radial plane at level L2 and which is fluidly connected to the flushing outlet 210 in the housing wall as well as to the upper end of each flushing groove 212a to 212d. This distribution channel is formed by the housing 200 and the valve member 300 in combination. More specifically, as shown in FIGS. 1e and 1f, the upper part of the outer valve member surface 302, above inlet 322, terminates in an outwardly flaring, circumferential concave neck 308. In the assembled state of the valve, the circular flushing fluid channel 213 is formed at level L2 between the concave surface of the neck 308 and the inner surface 204 of the housing 200. Thereby, the flushing fluid entering at the flushing inlet F will be present at each one of the flushing grooves 212a to 212d (see e.g. FIG. 1y).

In the assembled state of the valve 100, the single inlet 322 of the valve member 300 is located at the same level L1 as the bottom part of the flushing grooves 212a to 212d receiving the flushing fluid. The bottom part of the flushing grooves 212a to 212d may be considered to constitute flushing fluid outlets 210 of the housing. Thus, by rotation of the handle 304, the single inlet 322 of the valve member 300 may be brought into alignment with the fluid outlets 210 at the flushing grooves 212a to 212d for receiving the flushing fluid via the flushing inlet F.

Figure 1U:
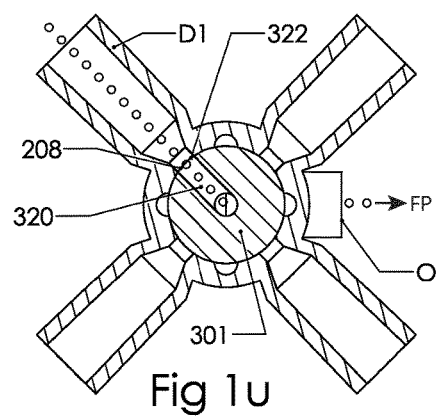

In the assembled valve 100, the single inlet 322 of the valve member 300 is located at the same level L1 as the drug outlets 208 in the housing 200, as shown in FIG. 1u). Thus, by rotation of the handle 304, the single inlet 322 may be brought in alignment with the drug outlets 208 for receiving the different drugs via the drug inlets D1 to D4.

The actual geometrical design of the channel 320 inside the valve member 300 may not be critical and may differ from the 90 degree bend configuration shown. The positions of the single inlet 322 and the single outlet 324 of the passageway 320 are more important.

In the assembled valve, the resilient lip 224 at the housing bottom is operatively engaged with a contoured circumferential surface 310 of a bottom groove 312 of the valve member 300 (FIGS. 1f and 1h) in order to provide a tactile response to the user when the valve member is rotated into one of the four drug positions or the four flushing positions.

In some embodiments, the contoured circumferential surface 310 and the resilient lip 224 may be formed as a protrusions, notches, grooves or recesses with smooth or sharp edges to create a forced clockwise rotation, or a forced clockwise rotation with a possibility to turn one position back from a flushing position to a previous drug position.

The operation of the valve in FIG. 1 will now be described with reference to FIGS. 1j to 1o showing first one of four possible flushing positions, FIGS. 1p to 1u showing one of four possible drug positions, and FIGS. 1v to 1aa showing a second one of four possible flushing positions.

FIGS. 1j to 1o illustrate one of four possible flushing positions of the valve 100. Flushing is typically performed after having administered a drug in order (i) to ensure that all drug fluid present in the valve is administered to the patient, (ii) to flush the valve member and the infusion tube downstream the valve from any residual drugs and (iii) to prevent bacteria growth in the valve.

Thus, if no drug yet has been administered through the valve, this position may also be considered as a priming position. However, the term flushing position will be used also for positions where priming is intended. Priming is normally performed at an initial stage in order to remove air from the valve, and from the tubings downstream the valve.

The initial flushing also serves to prepare the veins for the infusion to verify that the infusion is working properly.

In the illustrated $1^{st}$ flushing position, the handle 304 is aligned with the flushing inlet F and flushing groove 212a (FIG. 1j). In this position, the single channel inlet 322 of the valve member 300 is aligned with the flushing outlet 210 (FIG. 1o). A flushing fluid entering the valve at the flushing inlet F may then flow through the valve along the following flow path FP indicated in the cross sectional views in FIGS. 1m to 1o:

Flushing inlet F→Down along flushing groove 212a
  to level L1→Flushing outlet 210→Inlet opening
  322→Fluid passageway 320→Outlet opening
  324→Bottom opening 222→Bottom channel
  220→Outlet O FIGS. 1p to 1u illustrate one of four possible drug positions of the valve 100. As shown by arrow 402, the valve member 300 has now been rotated 45 degrees clockwise into alignment with the drug inlet D1. In this position, the single channel inlet 322 of the valve member 300 is aligned with the outlet 208 of the drug inlet D1. A first drug fluid entering the valve at the drug inlet D1 may then flow through the valve along the following flow path indicated in the cross sectional views in FIGS. 1t and 1u:

Drug inlet D1→Drug outlet 208 at level L1→Inlet
  opening 322→Fluid passageway 320→Outlet
  opening 324→Inlet opening 222→Bottom channel 220→Outlet O When the administration of the first drug fluid at drug inlet D1 has been terminated, and a subsequent drug fluid (at drug inlet D2) in the sequence should be administered to the patient, the handle 304 is rotated clockwise as indicated by arrows 404 and 406.

The valve member 300 will now first reach the subsequent second flushing position as indicated by arrow 404 and illustrated in FIGS. 1v to 1aa. Thus, the valve member 300 cannot be moved from the first drug position (D1) to the next drug position (D2) as indicated by dashed arrow 406 without passing a flushing position.

In this subsequent second flushing position, the single channel inlet 322 of the valve member 300 is aligned with the next flushing groove 212b and the flow path of the flushing fluid will be as follows:

Flushing inlet F→Circular distribution channel 213
  at level L2→Down along flushing groove 212b
  to level L1→Flushing outlet 210→Inlet opening
  322→Fluid passageway 320→Outlet opening
  324→Bottom opening 222→Bottom channel
  220→Outlet O It will especially be noted that the flushing fluid and the drug fluid will follow the same flow path in passageway 320 through the valve member 300. Thus, the flushing fluid will now efficiently remove any residuals of the first drug fluid from the channel passageway 320 before the next drug in the sequence is administered via drug inlet D2.

With reference to the indicated flowpath FP in FIG. 1y, it will be noted that the flushing fluid will actually be present circumferentially in the whole channel 213 and not only at the part indicated by the flowpath on level L2 as in the figure.

When the flushing has been terminated in the second flushing position in FIGS. 1v to 1aa, the valve member 300 will be rotated further clockwise as indicated by dashed arrow 406 to the next drug position D2.

Having the drug inlets D1 to D4 distributed over 360 degrees may provide the following advantages:

The inlets are distributed with maximum angular space to improve the sealing capability by using as much sealingly area as possible.

The inlets are distributed with maximum angular space to improve space for the operators' finger and thumb.

Fully closed valve positions may be arranged between the flushing positions and the drug positions.

In the following, a number of alternative embodiments will be described with reference to FIGS. 2 to 4. Same reference numerals will be used for the same or similar parts. To the extent the structure and operation is the same as for the embodiment in FIG. 1 no description will be given.

Second Embodiment of a 4-Drug Valve (FIG. 2)

The embodiment of the valve 300 in FIG. 2 also comprises four drug positions and four intermediate flushing positions. The positions and levels of the drug inlets D1 to D4, the flushing inlet F and the outlet O are the same as in FIG. 1. The operation by the user is also the same.

Figure 2A:
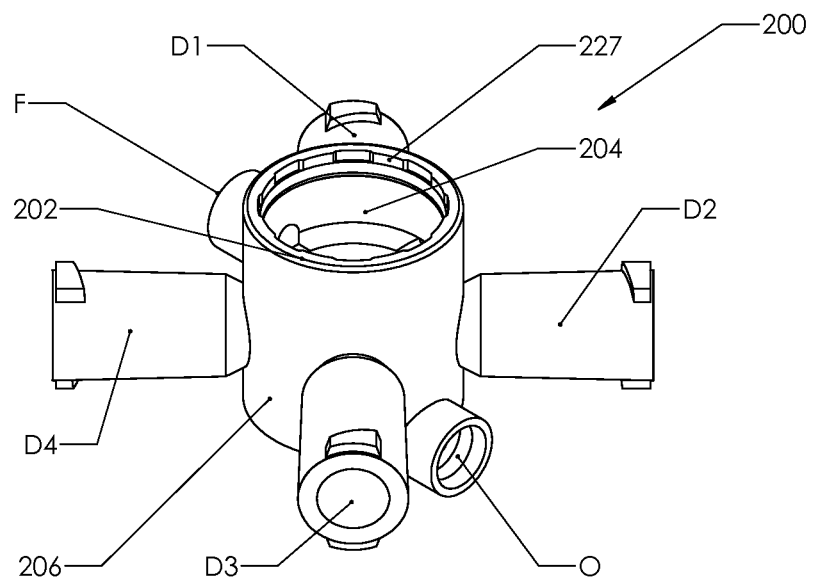
FIG. 2 illustrates a second embodiment of a 4-drug valve.
Figure 2B:
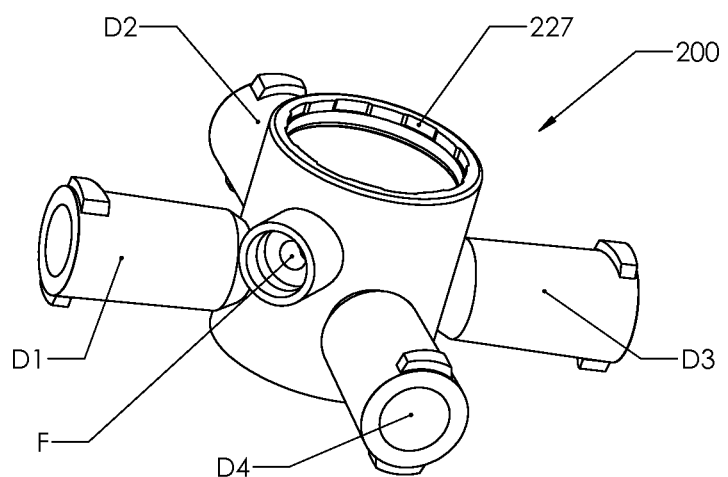
Figure 2C:
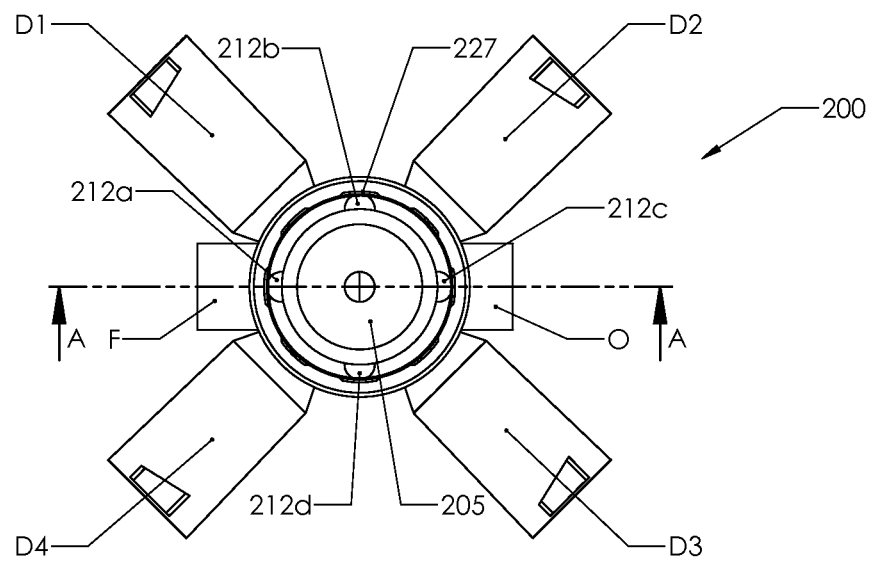
Figure 2D:
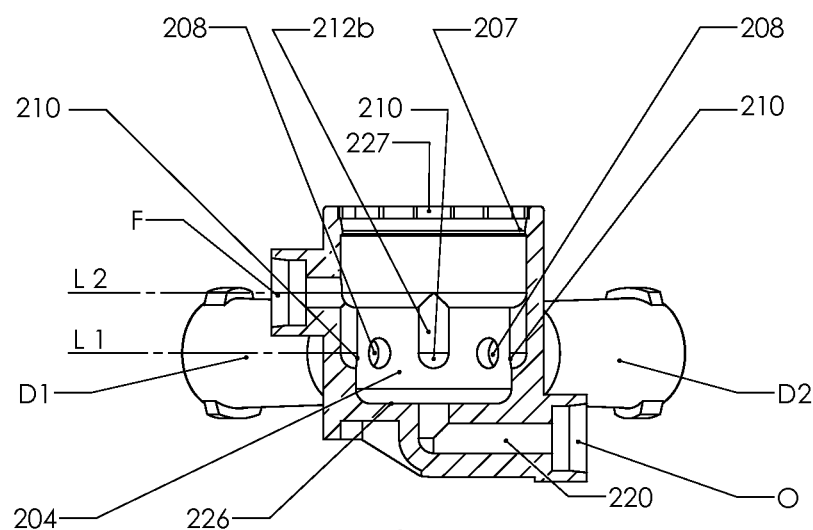
Figure 2E:
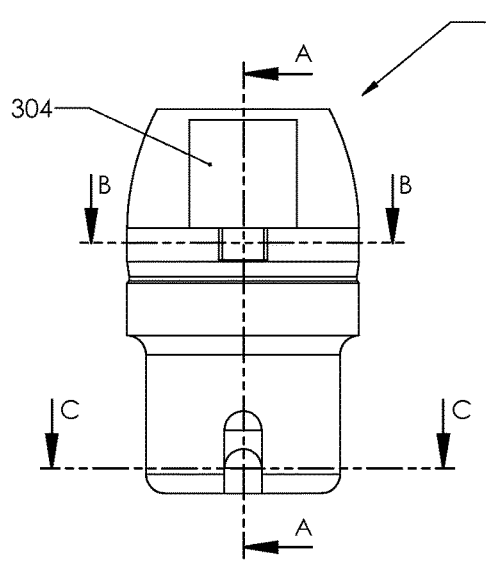
Figure 2F:
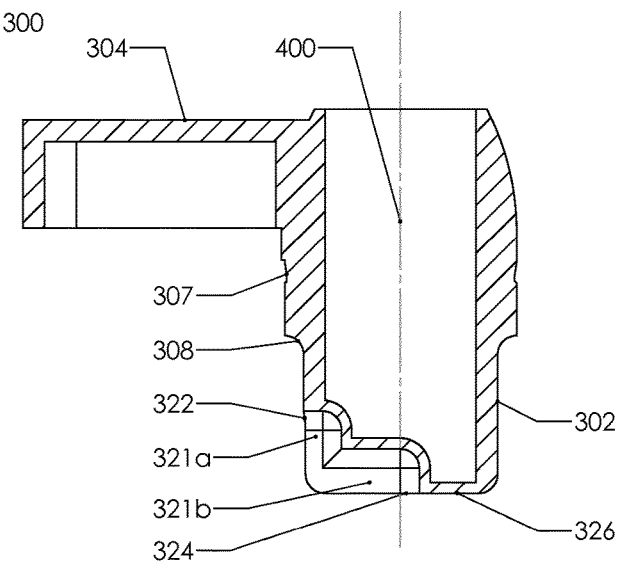

The main difference compared to FIG. 1 is that the tubular channel 320 in FIG. 1 forming the passageway 320 through the valve member 300 is replaced by an open recess or groove 321 formed by an axial part 321*a* and a radial part 321*b* at the bottom of the valve member 300 (FIG. 2*f*). In the assembled valve, a fluid passageway is formed by this open groove 321 in combination with the inner circumferential surface 204 of the housing 200 and the bottom surface 226 of the housing 200 (FIG. 1*n*).

Figure 2G:
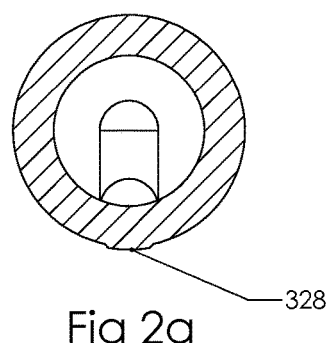
Figure 2H:
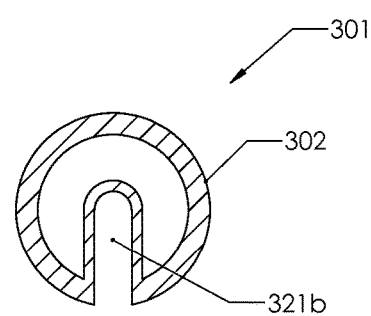
Figure 2I:
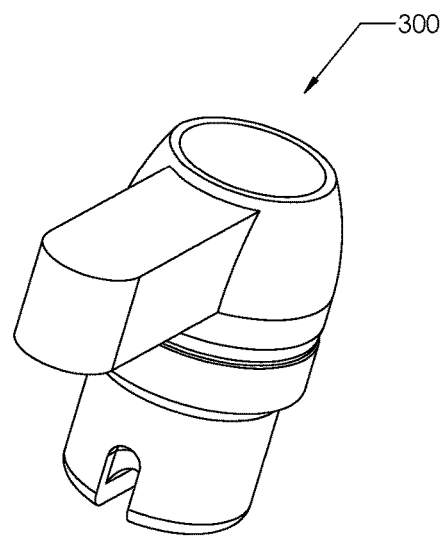
Figure 2P:
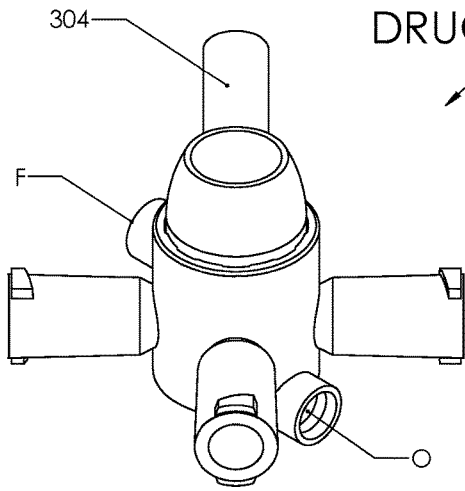
Figure 2Q:
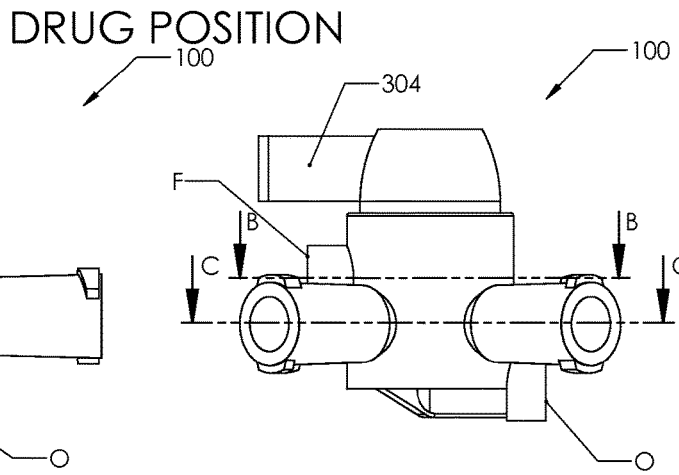
Figure 2R:
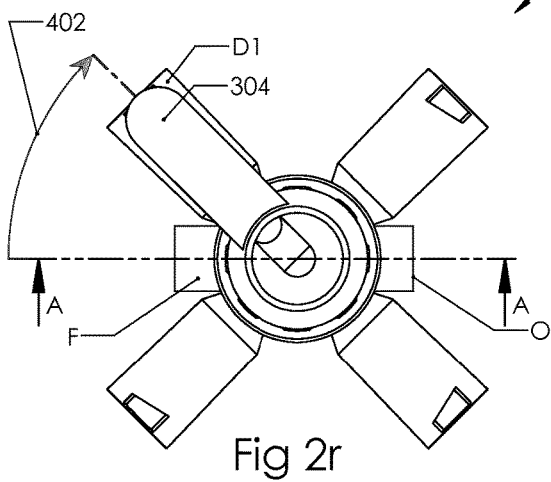
Figure 2S:
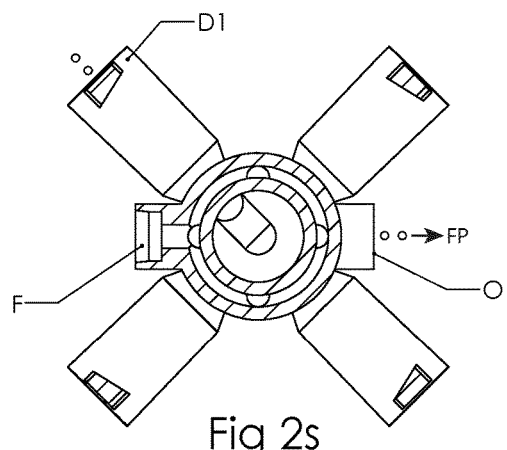
Figure 2T:
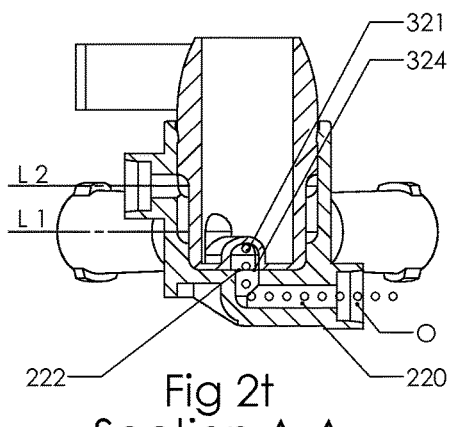
Figure 2U:
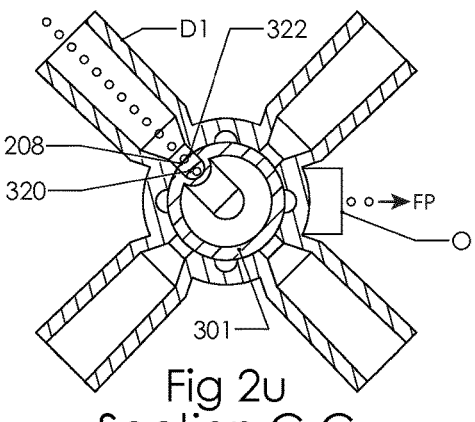

Another difference in relation to the embodiment in FIG. 1 is that the means for providing the tactile response are formed by a contoured surface 227 arranged at the top rim of the housing 200 and operatively engaged by a radially extending protrusion 328 formed on the outer surface of the valve member 300 (FIG. 2*g*).

As mentioned in connection with the previous embodiment in FIG. 1, in some embodiments, the contoured surface 227 and the protrusion 328 may be formed to create a forced clockwise rotation, or a forced clockwise rotation with a possibility to turn one position back from a flushing position to a previous drug position.

From a manufacturing point of view, a cylindrical housing may be designed with an open bottom or a closed bottom. An open bottom makes it possible to make a feathered feature as a tactile response, with a mould tool from below. An open bottom also makes it possible to create a larger flange or a rim in the tooling split line, because of a mould tool from below. More complex design may be achieved with an open bottom. A closed bottom on the other hand may result in a simpler valve member, where valve member and its passageway is created with two moulds only.

Third Embodiment of a 4-Drug Valve (FIG. 3)

The embodiment of the valve 300 in FIG. 3 also comprises four drug positions and four intermediate flushing positions.

The main differences compared to the embodiment in FIG. 1 are as follows:

The drug inlets D1 to D4 at level L1 are less angularly spaced and are all positioned within a 165 degree angle.

The sealingly engaged surfaces 204 and 302 of the housing and the valve member are frusto-conical, tapering towards the bottom of the valve.

The flushing inlet F is located at a level L2 below the level L1 of drug inlets D1 to D4.

The bottom part of the flushing grooves 212*a* to 212*e* are located at level L2 where they are permanently fluidly connected to a circular distribution channel 213 in the assembled state of the valve. The flushing fluid entering at flushing inlet F will access this distribution channel 213. Thereby, the flushing fluid will be present in all of the flushing grooves 212*a* to 212*e* and thus accessible at level L1 in the respective flushing positions.

Figure 3A:
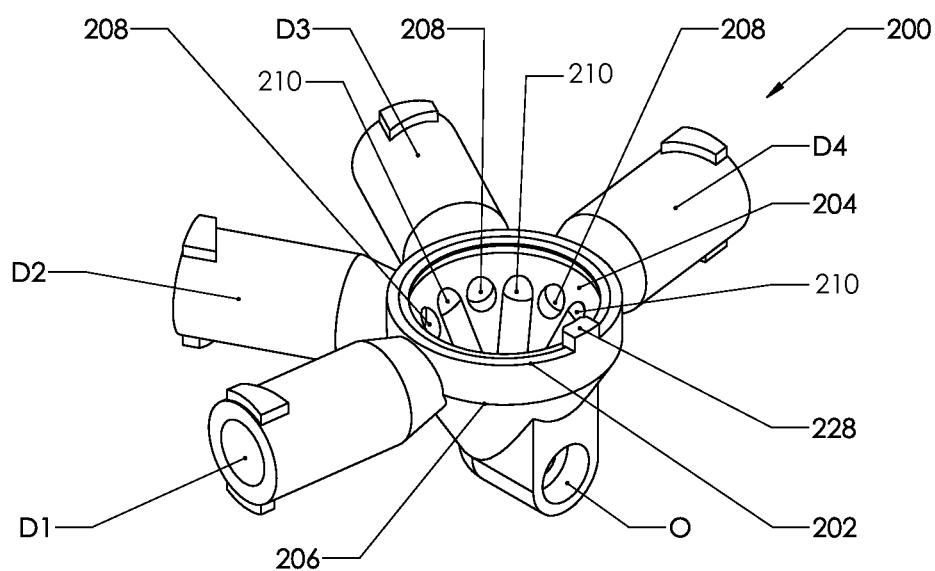
FIG. 3 illustrates a third embodiment of a 4-drug valve.
Figure 3B:
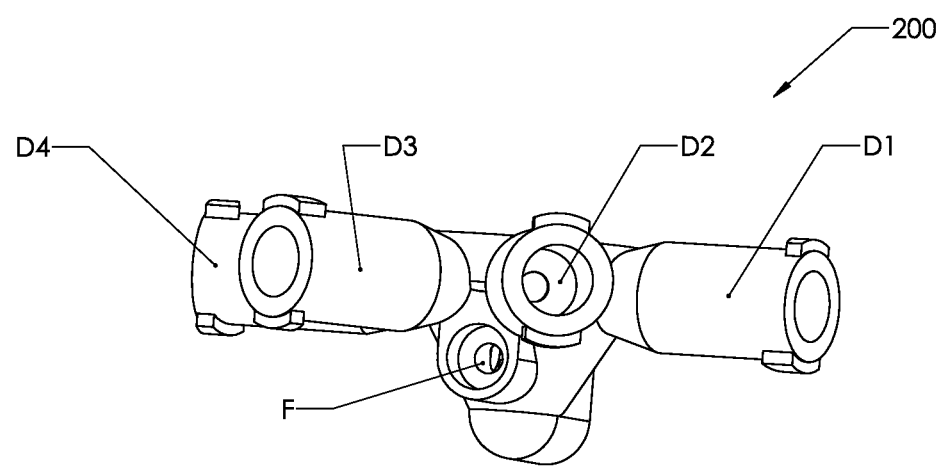
Figure 3C:
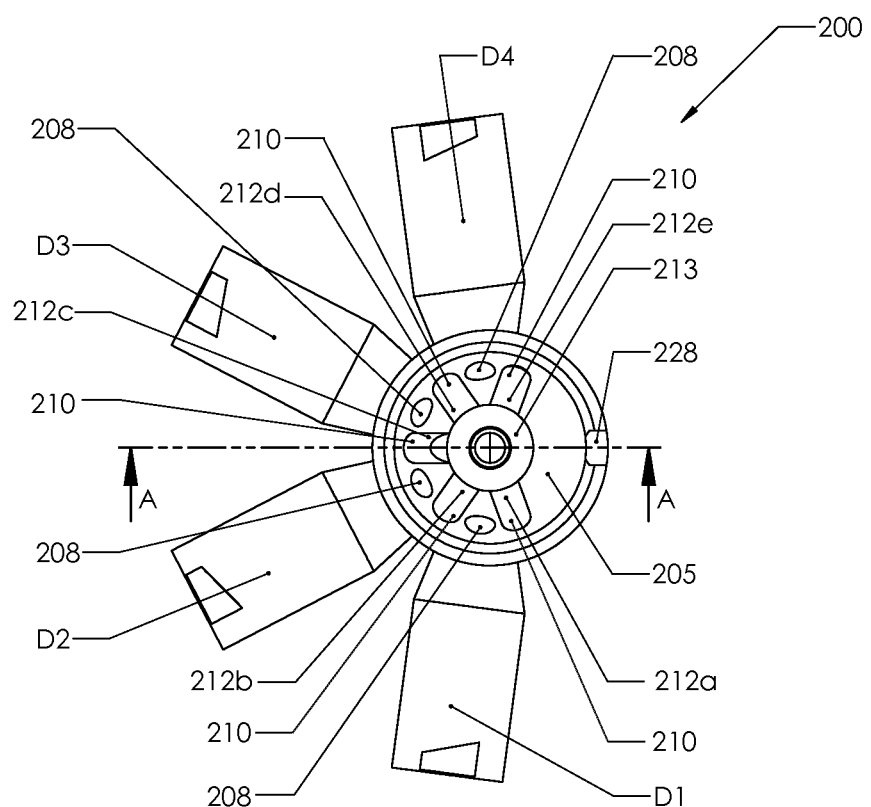
Figure 3D:
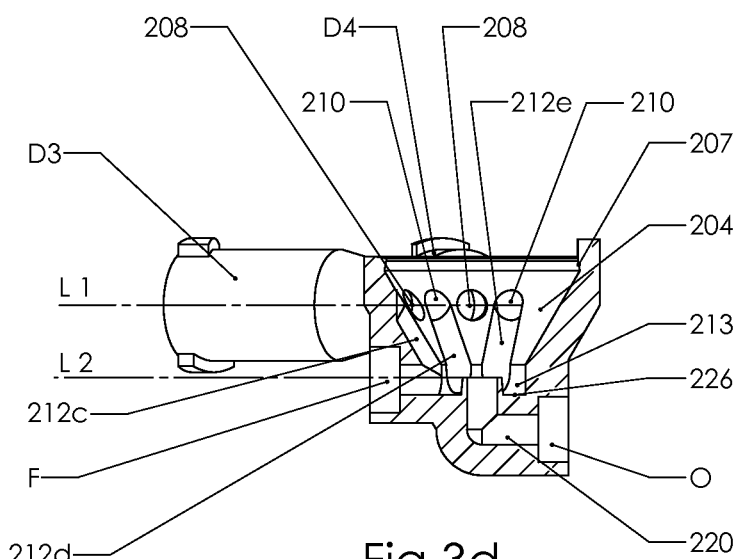
Figure 3E:
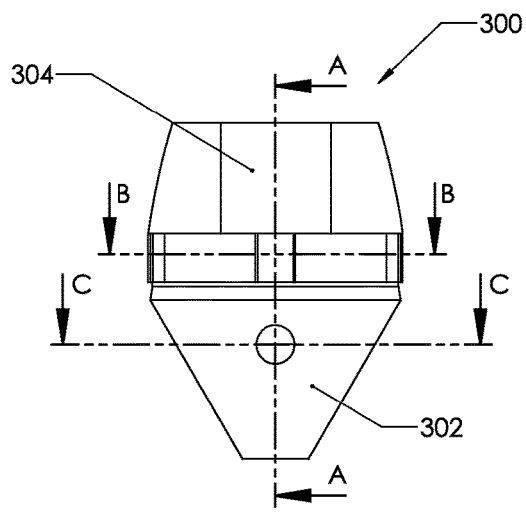
Figure 3F:
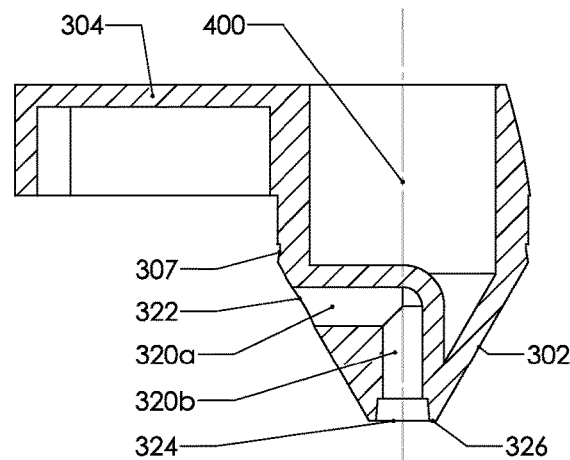
Figure 3G:
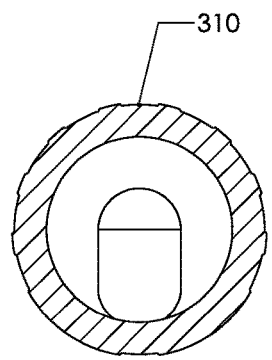
Figure 3H:
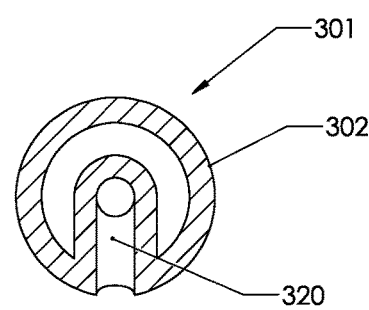
Figure 3I:
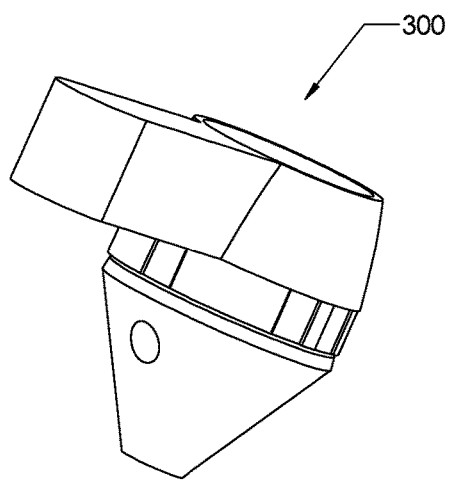
Figure 3J:
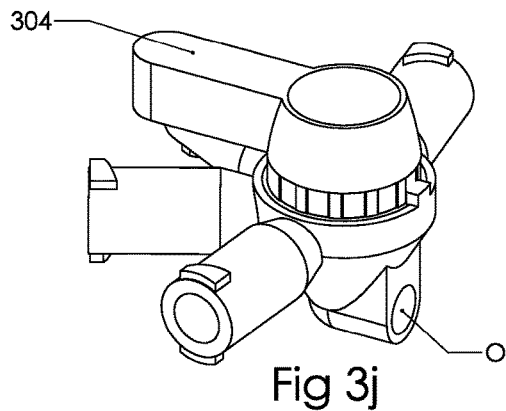
Figure 3K:
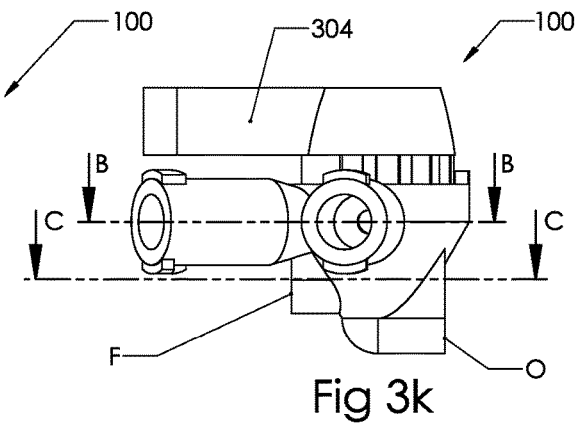
Figure 3L:
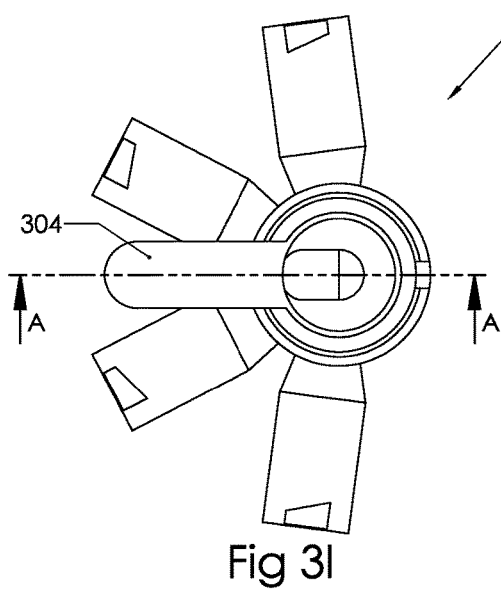
Figure 3M:
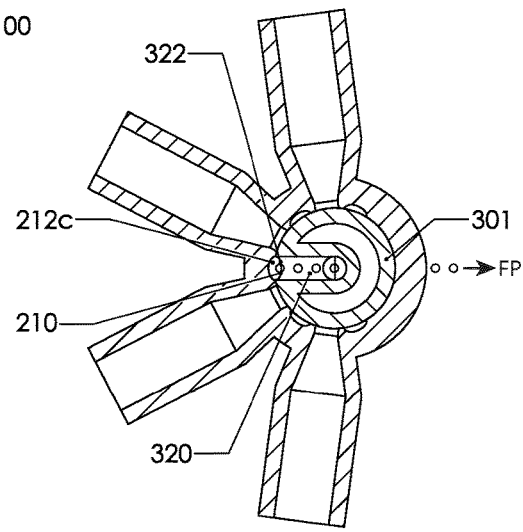
Figure 3N:
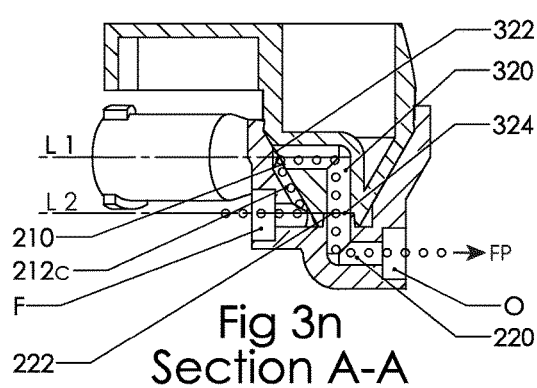
Figure 3O:
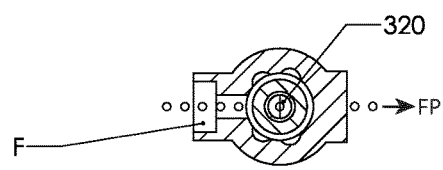
Figure 4A:
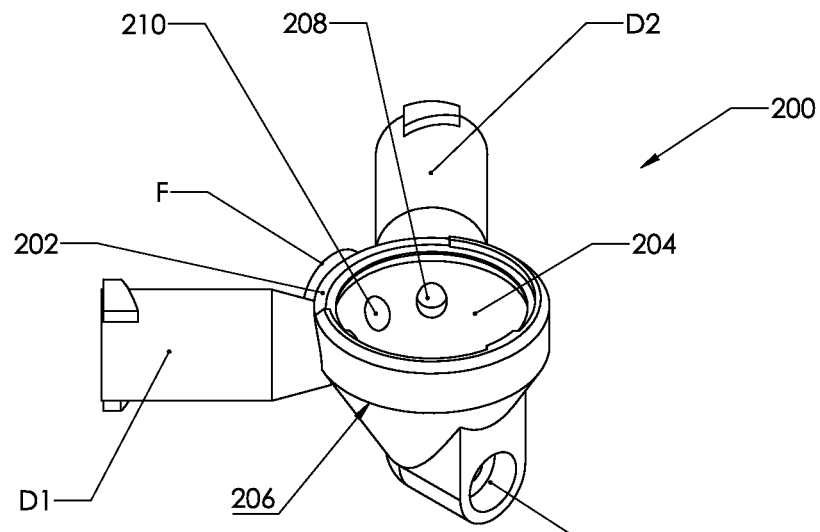
FIG. 4 illustrates an embodiment of a 2-drug valve.
Figure 4B:
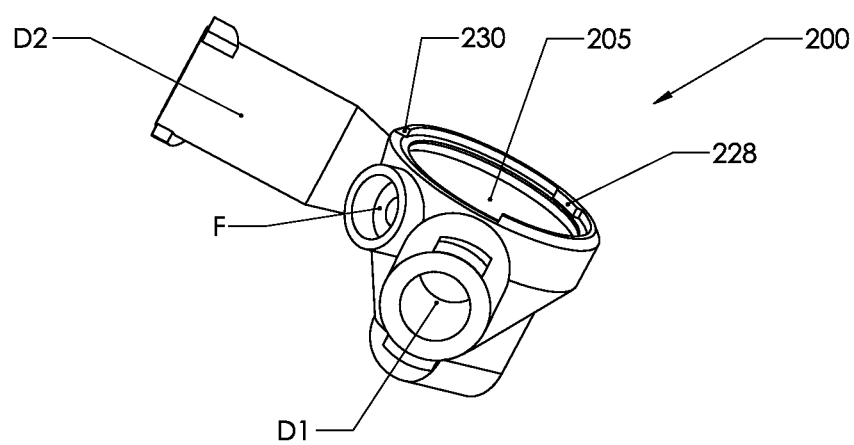
Figure 4C:
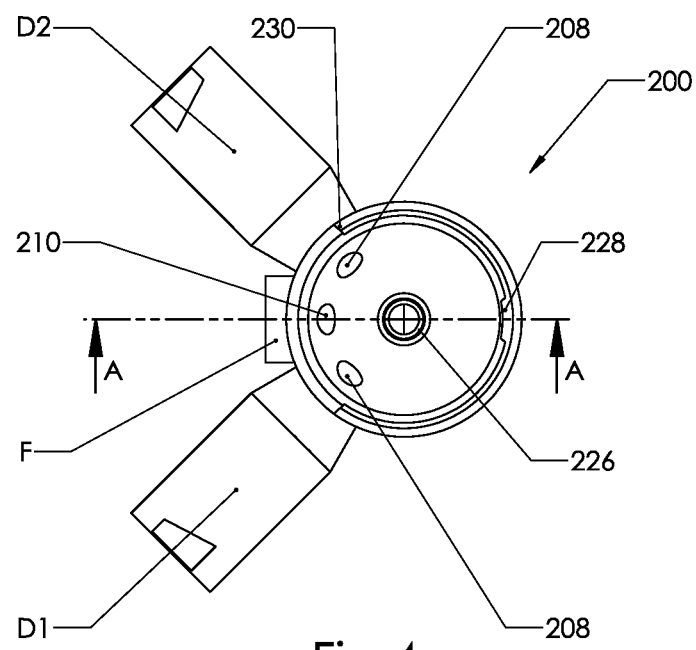
Figure 4D:
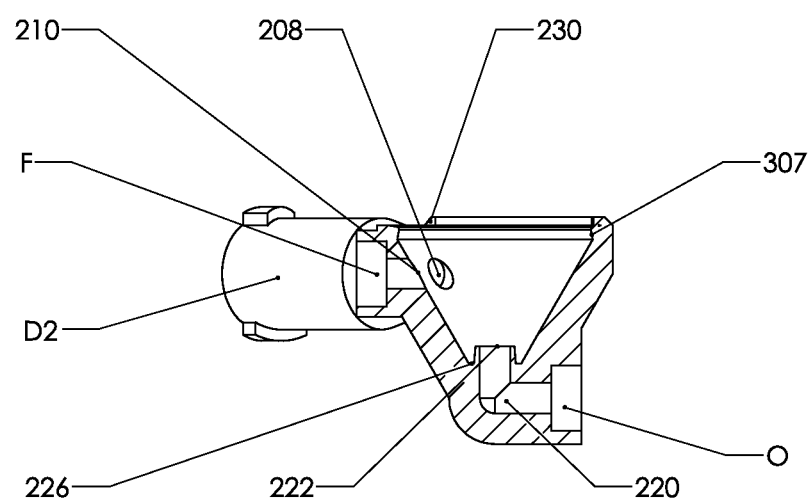
Figure 4E:
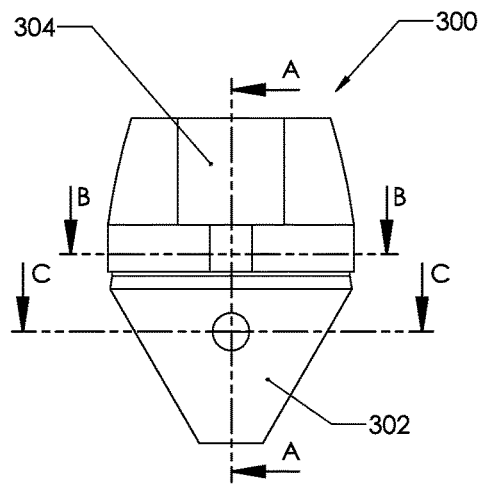
Figure 4F:
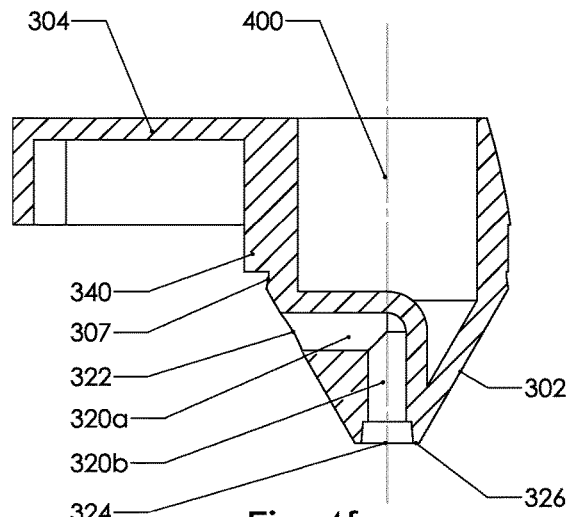
Figure 4G:
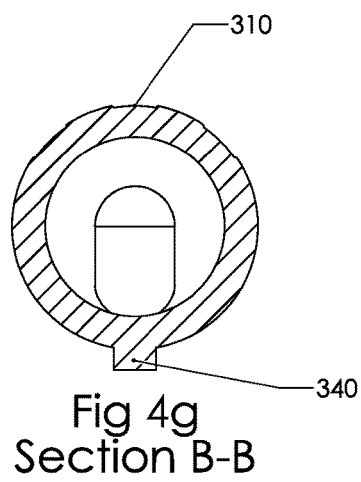
Figure 4H:
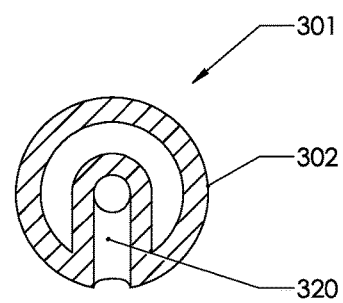
Figure 4I:
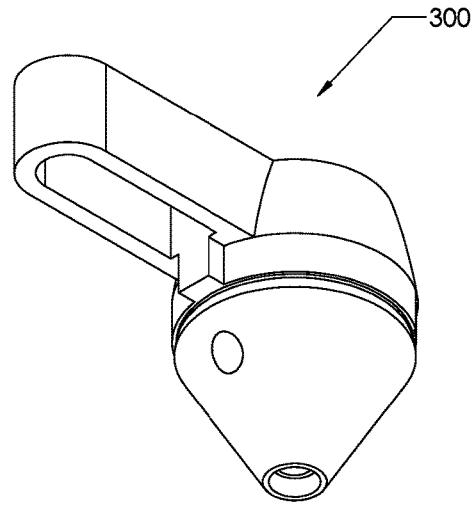
Figure 4J:
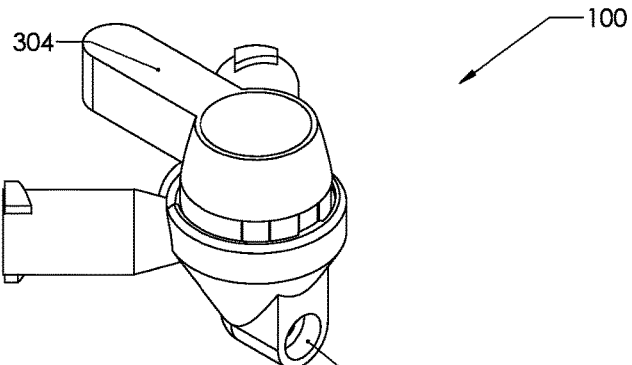
Figure 4K:
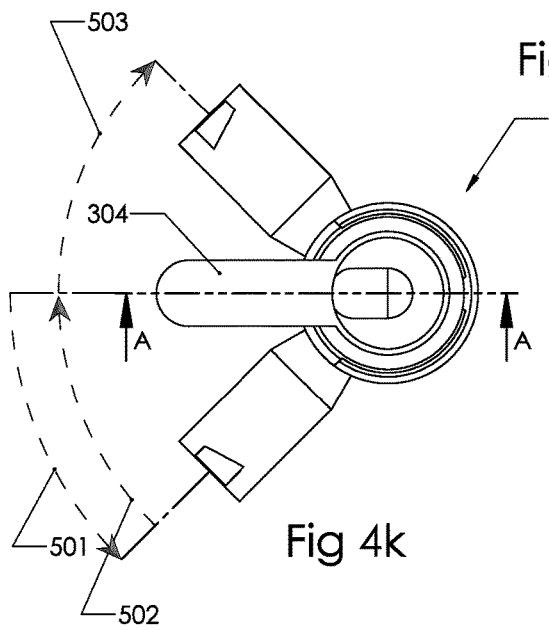
Figure 4L:
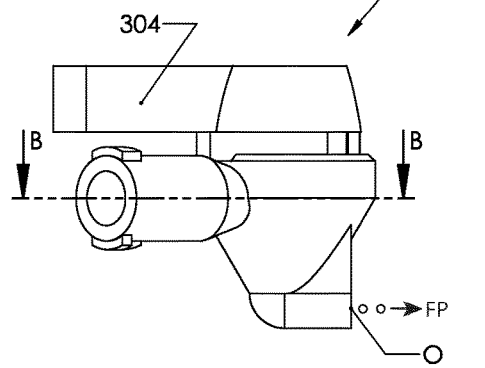
Figure 4M:
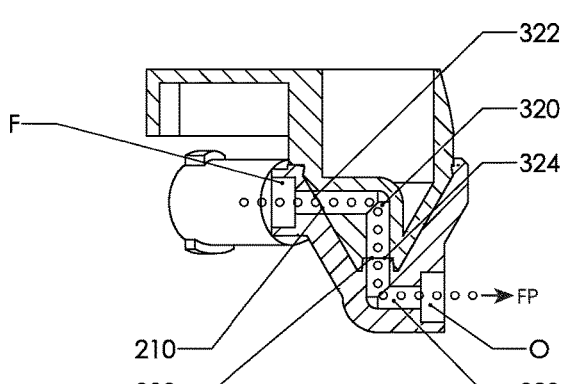
Figure 4N:
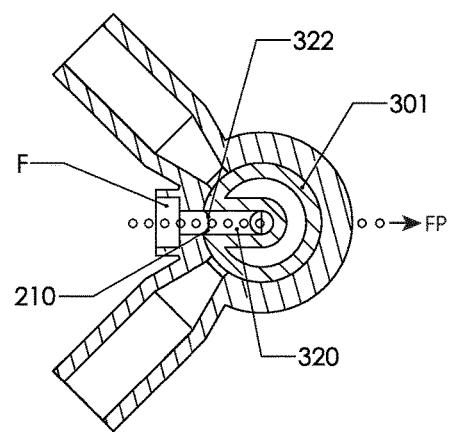
Figure 4O:
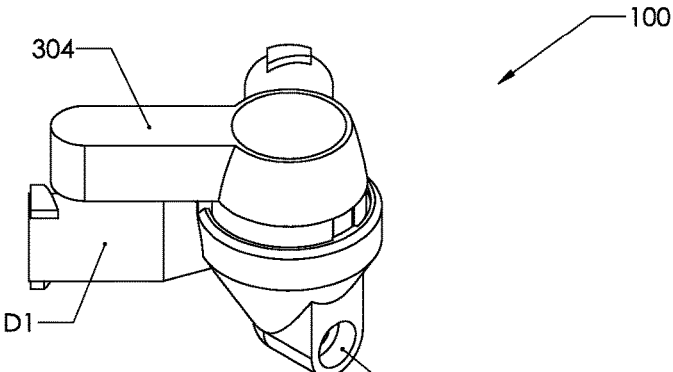
Figure 4P:
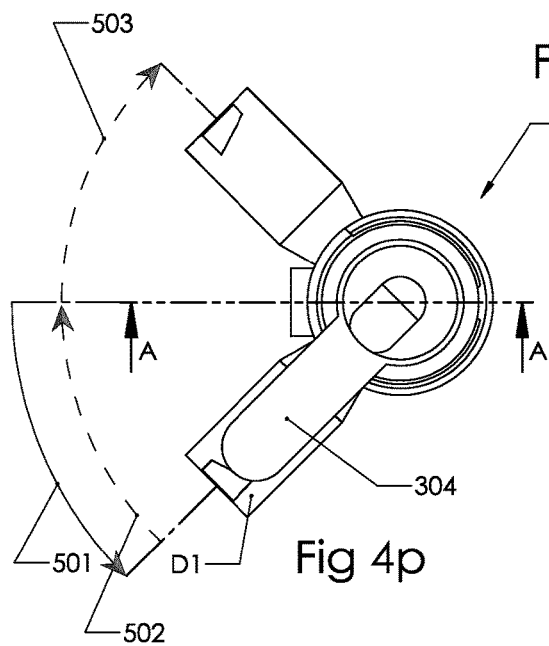
Figure 4Q:
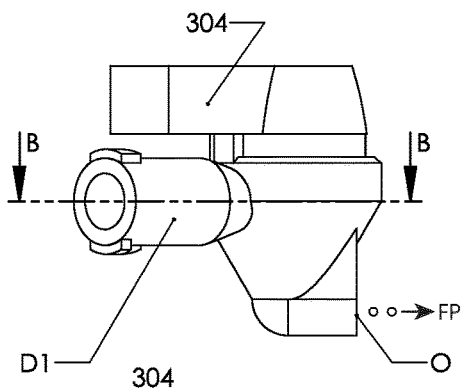
Figure 4R:
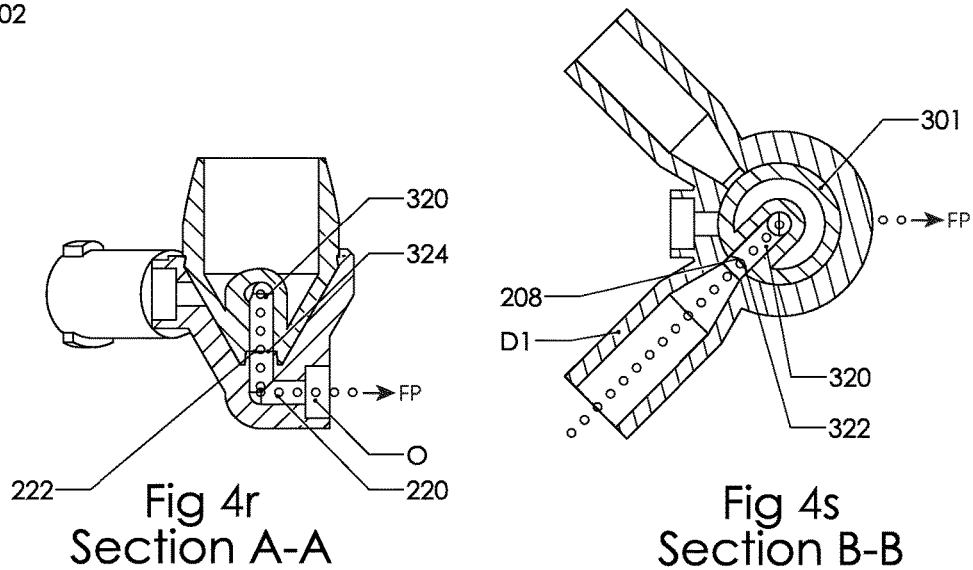
Figure 4S:
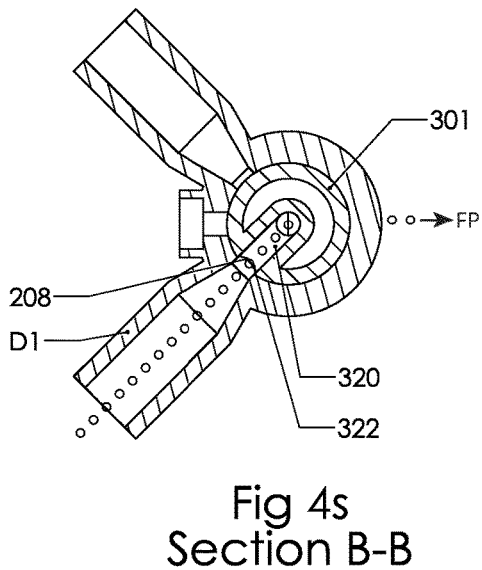

FIGS. 3*j* to 3*o* illustrate a flushing position of the valve in FIG. 3 with the handle 304 aligned with flush inlet F (between drug inlets D2 and D3) and aligned with flushing groove 212*c*. The flow path FP in this flushing position will be as follows:

Flushing inlet F→Up along inclined flushing groove 212*c* to level L1→Flushing outlet 210→Inlet opening 322→Down through passageway channel 320→Outlet opening 324→Bottom channel 220→Outlet O FIGS. 3*v* to 3*aa* illustrate a second flushing position of the valve in FIG. 3 where the handle 304 has been turned passed via a drug position (arrow 402; FIGS. 3*p* to 3*u*) to a subsequent flushing position (arrow 404).

In this position, the distribution channel 213 is now "active" (FIG. 3*aa*). The flow path FP in the subsequent flushing position will be as follows:

Flushing inlet F→Into flushing channel 213 at level L2→Along circular flushing channel 213 at level L2 to the bottom of flushing groove 212*d*→Up along inclined flushing groove 212*d* to level L1→Flushing outlet 210 at level L1→Inlet opening 322→Down through passageway channel 320→Outlet opening 324→Bottom channel 220→Outlet O A conical embodiment according to FIG. 3 may present the following advantages Reduced housing volume saves material.

Large sealing surface of the housing.

Large sealing surface of the valve member.

The annular channel 213 and the recesses 212 are formed without the need of altering the smooth surface of the valve member which improves sealing capability.

The embodiment in FIG. 3 may present the following further advantages:

Considering that the valve in use would normally be suspended with its rotational axis horizontal and the inlets pointing upwards, residual drugs would be minimized in the drug inlets and drug tubing, since drugs in the tubing and inlets flow downwards by means of gravity force.

There is less kink of the drug tubings since drug inlets point upwards toward the infusion bags in use.

The drug tubings may be shorter since drug inlets point upwards towards the infusion bags.

An optional advantage could be that the valve may present a rather extended closed position (where there are no inlets). Such a no-flow position may be used at delivery and/or during use and/or during disposal after use.

First Embodiment of a 2-Drug Valve (FIG. 4)

The embodiment of the valve 300 in FIG. 4 is conical as the embodiment in FIG. 3 and presents the following specific features:

There are only two drug inlets D1 and D2 arranged in a V configuration and corresponding to two drug positions.

The flushing inlet is arranged at the same level as the drug inlets D1 and D2.

There is only one single intermediate flushing position. Thus, there is no need for any circular distribution channel for the flushing fluid.

The two drug outlets 208 and the single flushing outlet 210 are all located at the same level as the inlet 322 of the valve member 300.

The fluid passageway in the valve member 300 is in the form of a tubular channel 320.

The valve is provided with means 230 and 340 for limiting the rotation of the valve member such that the user cannot go from one drug position to the other drug position without passing the flushing position.

In use, the valve member will be rotated in both directions.

In use of a valve according to FIG. 4, after a possible initial priming in the position shown in FIGS. 4*j* to 4*n*, the valve member 300 is rotated counter-clockwise as indicated by arrow 501 to the first drug position shown in FIGS. 4*o* to 4*s*. Thereafter, the valve member is rotated clockwise as indicated by arrow 502 back to the flushing position for removing any residuals of the first drug from the fluid passageway 320. As in the previous embodiments, the flow path through the valve member 300 will be the same for the drugs and the flushing fluids. Thereafter, the valve member 300 will be rotated further clockwise to the second drug position as indicated by arrow 503.

The invention claimed is:

1. A valve for administration of two or more drug fluids comprising:
 a valve housing having:
  an inner circumferential surface,
  a plurality of drug inlets for receiving said drug fluids and fluidly connected to associated drug outlets of the housing; and
  one flushing inlet for receiving a flushing fluid and fluidly connected to one or more flushing outlets of the housing; wherein said plurality of drug outlets of the housing and said one or more flushing outlets of the housing are all arranged at the inner circumferential surface of the housing on a common axial level; and
 a valve member having a rotational axis and provided with a passageway presenting a single inlet arranged on said common axial level relative to said rotational axis at an outer circumferential surface of the valve member, and a single outlet arranged coaxially with said rotational axis;
 wherein the valve is arranged such that the valve member can be rotated into:
  a plurality of drug positions in each of which the single passageway inlet is aligned with and fluidly connected to a respective one of said drug outlets for guiding an associated drug fluid via a flow path defined by said passageway to said passageway outlet, and
  one or more flushing positions in which the single passageway inlet is aligned with and fluidly connected to a respective one of said one or more flushing outlets for guiding said flushing fluid through the same flow path defined by said passageway in order to flush said passageway from any drug residuals, and
 wherein the valve member is prevented from rotating from one drug position to another drug position without passing one of said flushing positions.

2. The valve according to claim 1, wherein said one or more flushing outlets comprises a plurality of flushing outlets defining the same plurality of flushing positions, and wherein said one flushing inlet is fluidly connected to each one of said plurality of flushing outlets.

3. The valve according to claim 2, wherein the flushing inlet is fluidly connected to said plurality of flushing outlets via an annular flushing fluid distribution channel.

4. The valve according to claim 3, further comprising a plurality of flushing grooves formed in the inner circumferential surface of the valve housing, said flushing grooves extending at least partly in the direction of the rotational axis and being fluidly connected to a respective one of said plurality of flushing outlets and to said annular flushing fluid distribution channel.

5. The valve according to claim 4, wherein said circumferential inner surface of the housing and said circumferential outer surface of the valve member are cylindrical.

6. The valve according to claim 1, wherein the outer circumferential surface of the valve member is sealingly engaged with the inner circumferential surface of the housing.

7. The valve according to claim 1, wherein the passageway of the valve member comprises, in the flow direction, a first part extending from the inlet of the passageway towards the rotational axis, and a second part extending coaxially with the rotational axis from a radially inner end of the first part towards the channel outlet opening.

8. The valve according to claim 1, wherein the valve member is prevented from rotating from one drug position to another drug position without passing a flushing position by the provision of rotational stop means limiting the rotational movement of the valve member.

9. The valve according to claim 1, wherein the valve member is prevented from rotating from one drug position to another drug position without passing a flushing position by the provision the same number of flushing positions as the number of drug positions, said flushing positions being interlaced with the drug positions.

10. The valve according to claim 1, wherein valve member is prevented from rotating from one drug position to another drug position without passing a flushing position by the provision of a higher number of flushing positions than the number of drug positions, said flushing positions being interlaced with the drug positions and at both ends of the administration sequence.

11. The valve according to claim 1, wherein said circumferential inner surface of the housing and said circumferential outer surface of the valve member are cylindrical.

12. The valve according to claim 1, wherein said circumferential inner surface of the housing and said circumferential outer surface of the valve member are frusto-conical.

13. The valve according to claim 1, further comprising means for providing a tactile response to a user at each of said drug and flushing positions.

* * * * *